United States Patent
Sheppard et al.

(10) Patent No.: US 7,253,261 B2
(45) Date of Patent: *Aug. 7, 2007

(54) INTERFERON-LIKE PROTEIN ZCYTO21

(75) Inventors: Paul O. Sheppard, Granite Falls, WA (US); Scott R. Presnell, Tacoma, WA (US); Brian A. Fox, Seattle, WA (US); Teresa Gilbert, Seattle, WA (US); Betty A. Haldeman, Seattle, WA (US); Francis J. Grant, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 523 days.

This patent is subject to a terminal disclaimer.

(21) Appl. No.: 10/927,815

(22) Filed: Aug. 27, 2004

(65) Prior Publication Data

US 2005/0106682 A1 May 19, 2005

Related U.S. Application Data

(62) Division of application No. 09/895,834, filed on Jun. 29, 2001, now Pat. No. 6,927,040.

(60) Provisional application No. 60/285,424, filed on Apr. 20, 2001, provisional application No. 60/215,446, filed on Jun. 30, 2000.

(51) Int. Cl.
*C07K 14/52* (2006.01)
*C12N 15/20* (2006.01)
*C12P 21/00* (2006.01)

(52) U.S. Cl. .................. 530/351; 435/69.51; 435/70.1; 435/325; 424/85.4

(58) Field of Classification Search .................... None
See application file for complete search history.

(56) References Cited

FOREIGN PATENT DOCUMENTS

| EP | 0 032 124 | 7/1981 |
|---|---|---|
| WO | 02/092762 | 11/2002 |
| WO | 03/066002 | 8/2003 |

OTHER PUBLICATIONS

Adams et al., Accession No. T07139, 1993.
DOE Joint Genome Institute Stanford Human Genome Center, Accession No. AC011445, 1999.
Muzney et al., Accession No. AC0118477, 1999.
Sanger Centre Search Results, Accession No. AC011445, 2001.
University of California Santa Cruz database using Softberry, Inc. gene prediction software, Accession No. C19001084, 2001.
Scott et al., "The Pendred syndrome gene encodes a chloride-iodide transport protein," *Nature Genetics*, 21:440-443, 1999.
Korba et al., "A cell culture assay for compounds which inhibit hepatitis B virus replication," *Antiviral Research 15*:217-228, 1991.
Korba et al., "Use of a standardized cell culture assay to assess activities of nucleoside analogs against hepatitis B virus replication," *Antiviral Research 19*:55-70, 1992.
Kotenko et al., "IFN-λs mediate antiviral protection through a distinct class II cytokine receptor complex," *Nat. Immunol. 4*(1):69-77, 2003.
Sheppard et al., "IL-28, IL-29 and their class II cytokine receptor IL-28R," *Nat. Immunol. 4*(1):63-68, 2003.
Brack et al., "Molecular analysis of the human interferon-α gene family," *Gene 15*:379-394, 1981.

*Primary Examiner*—Christine J. Saoud
*Assistant Examiner*—Jegatheesan Seharaseyon
(74) *Attorney, Agent, or Firm*—Brian J. Walsh

(57) ABSTRACT

The present invention relates to polynucleotide and polypeptide molecules for Zcyto21, an interferon-like protein, which is most closely related to interferon-α at the amino acid sequence level. The present invention also includes antibodies to the Zcyto21 polypeptides, and methods of using the polynucleotides and polypeptides.

18 Claims, 6 Drawing Sheets

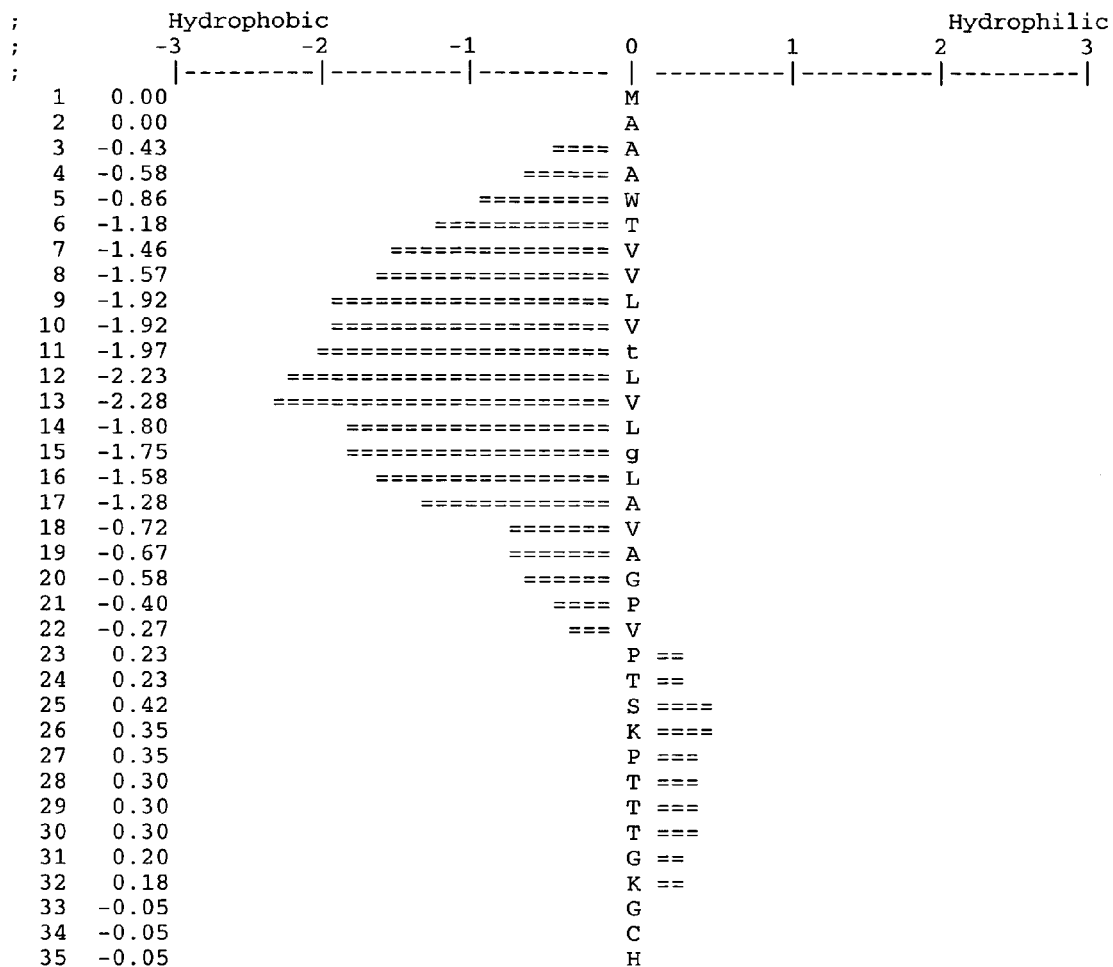
Figure 1 (sheet 1 of 6)

```
188    0.23                              D   ==
189    0.23                              L   ==
190    0.17                              C   ==
191   -0.28                         ===  L
192    0.06                              R   =
193    0.26                              T   ===
194    0.67                              S   =======
195    0.78                              T   =======
196    1.01                              H   =========
197    1.00                              P   =========
198    0.00                              E
199    0.00                              S
200    0.00                              T
;              |---------|---------|--------- |---------|---------|---------|
;             -3        -2        -1         0         1         2         3
;         Hydrophobic                                              Hydrophilic
;
```

INTERFERON-LIKE PROTEIN ZCYTO21

The present application is a divisional of U.S. patent application Ser. No. 09/895,834, filed Jun. 29, 2001, now U.S. Pat. No. 6,927,040, which claims the benefit under 35 U.S.C. §119(e) of U.S. provisional application Ser. Nos. 60/215,446, filed Jun. 30, 2000, and 60/285,424, filed Apr. 20, 2001, now abandoned all of which are herein incorporated by reference.

BACKGROUND OF THE INVENTION

Cellular differentiation of multicellular organisms is controlled by hormones and polypeptide growth factors. These diffusable molecules allow cells to communicate with each other and act in concert to form tissues and organs, and to repair and regenerate damaged tissue. Examples of hormones and growth factors include the steroid hormones, parathyroid hormone, follicle stimulating hormone, the interferons, the interleukins, platelet derived growth factor, epidermal growth factor, and granulocyte-macrophage colony stimulating factor, among others.

Hormones and growth factors influence cellular metabolism by binding to receptor proteins. Certain receptors are integral membrane proteins that bind with the hormone or growth factor outside the cell, and that are linked to signaling pathways within the cell, such as second messenger systems. Other classes of receptors are soluble intracellular molecules.

Cytokines generally stimulate proliferation or differentiation of cells of the hematopoietic lineage or participate in the immune and inflammatory response mechanisms of the body. Examples of cytokines which affect hematopoiesis are erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia, thrombocytopenia, and neutropenia or receiving chemotherapy for cancer. Cytokines play important roles in the regulation of hematopoiesis and immune responses, and can influence lymphocyte development.

The human class II cytokine family includes interferon-α (IFN-α) subtypes, interferon-β (IFN-β), interferon-γ (IFN-γ), IL-10, IL-19 (U.S. Pat. No. 5,985,614), MDA-7 (Jiang et al., *Oncogene* 11, 2477-2486, (1995)), IL-20 (Jiang et al., *Oncogene* 11, 2477-2486, (1995)), IL-22 (Xie et al., *J. Biol. Chem.* 275, 31335-31339, (2000)), and AK-155 (Knappe et al., *J. Virol.* 74, 3881-3887, (2000)). Most cytokines bind and transduce signals through either Class I or Class II cytokine receptors. Members of human class II cytokine receptor family include interferon-αR1 (IFN-αR1), interferon-γ-R2 (IFN-γ-R2), interferon-γ R1 (IFN-γ R1), interferon-γR2 (IFN-γR2), IL-10R (Liu et al., *J. Immunol.* 152, 1821-1829, (1994)), CRF2-4 (Lutfalla et al. *Genomics* 16, 366-373, (1993)), IL-20Rβ (Blumberg et al., *Cell* 104, 9-19, (2001)) (also known as zcytor7 (U.S. Pat. No. 5,945,511) and CRF2-8 (Kotenko et al., *Oncogene* 19, 2557-2565, (2000)), IL-20Rβ (Blumberg et al., ibid, (2001)) (also known as DIRS1 (PCT WO 99/46379)), IL-22RA1 (IL-22 receptor-α1, submitted to HUGO for approval) (also known as IL-22R (Xie et al., *J. Biol. Chem.* 275, 31335-31339, (2000)), zcytor11 (U.S. Pat. No. 5,965,704) and CRF2-9 (Kotenko et al., *Oncogene* 19, 2557-2565, (2000)), and tissue factor.

Class II cytokine receptors are typically heterodimers composed of two distinct receptor chains, the α and β receptor subunits (Stahl et al., *Cell* 74, 587-590, (1993)). In general, the α subunits are the primary cytokine binding proteins, and the β subunits are required for formation of high affinity binding sites, as well as for signal transduction. An exception is the IL-20 receptor in which both subunits are required for IL-20 binding (Blumberg et al., ibid, (2001)).

The class II cytokine receptors are identified by a conserved cytokine-binding domain of about 200 amino acids (D200) in the extracellular portion of the receptor. This cytokine-binding domain is comprised of two fibronectin type III (FnIII) domains of approximately 100 amino acids each (Bazan J. F. *Proc. Natl. Acad. Sci. USA* 87, 6934-6938, (1990); Thoreau et al., *FEBS Lett.* 282, 16-31, (1991)). Each FnIII domain contains conserved Cys, Pro, and Trp residues that determine a characteristic folding pattern of seven β-strands similar to the constant domain of immunoglobulins (Uze et al., *J. Interferon Cytokine Res.* 15, 3-26, (1995)). The conserved structural elements of the class II cytokine receptor family make it possible to identify new members of this family on the basis of primary amino acid sequence homology. Previously we have successfully identified two new members of class II cytokine receptor family, zcytor7 (U.S. Pat. No. 5,945,511) (also known as IL-20R α (Blumberg et al., ibid, (2001)) and zcytor11 (U.S. Pat. No. 5,965,704) (also known as IL-22R (Blumberg et al., ibid, (2001)), using this approach. Identification of additional novel members of the class II cytokine receptor family is of interest because cytokines play a vital role in regulating biological responses.

IL-22, also known as IL-TIF (IL-10-related T cell-derived inducible factor) (Dumoutier et al., *J. Immunology* 164, 1814-1819, (2000)), is a recently described IL-10 homologue. Mouse IL-22 was originally identified as a gene induced by IL-9 in T cells and mast cells in vitro (Dumoutier et al., *J. Immunology* 164, 1814-1819, (2000)). Acute phase reactant induction activity was observed in mouse liver upon IL-22 injection, and IL-22 expression was rapidly induced after lipopolysaccharide (LPS) injection, suggesting that IL-22 contributes to the inflammatory response in vivo (Dumoutier et al., *Proc. Natl. Acad. Sci. U.S.A.* 97, 10144-10149, (2000)).

The interleukins are a family of cytokines that mediate immunological responses, including inflammation. The interleukins mediate a variety of inflammatory pathologies. Central to an immune response is the T cell, which produce many cytokines and adaptive immunity to antigens. Cytokines produced by the T cell have been classified as type 1 and type 2 (Kelso, A. *Immun. Cell Biol.* 76:300-317, 1998). Type 1 cytokines include IL-2, IFN-γ, LT-α, and are involved in inflammatory responses, viral immunity, intracellular parasite immunity and allograft rejection. Type 2 cytokines include IL-4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

Of particular interest, from a therapeutic standpoint, are the interferons (reviews on interferons are provided by De Maeyer and De Maeyer-Guignard, "Interferons," in *The Cytokine Handbook, 3rd Edition*, Thompson (ed.), pages 491-516 (Academic Press Ltd. 1998), and by Walsh, *Biopharmaceuticals: Biochemistry and Biotechnology*, pages 158-188 (John Wiley & Sons 1998)). Interferons exhibit a variety of biological activities, and are useful for the treatment of certain autoimmune diseases, particular cancers, and the enhancement of the immune response against infectious agents, including viruses, bacteria, fungi, and protozoa. To date, six forms of interferon have been identified, which have been classified into two major groups. The so-called "type I" interferons include interferon-α, interferon-β, interferon-ω, interferon-δ, and interferon-τ. Currently, interferon-γ and one subclass of interferon-α are the only type II interferons.

Type I interferons, which are thought to be derived from the same ancestral gene, have retained sufficient similar structure to act by the same cell surface receptor. The α-chain of the human interferon-α/β receptor comprises an extracellular N-terminal domain, which has the characteristics of a class II cytokine receptor. Interferon-γ does not share significant homology with the type I interferons or with the type II interferon-α subtype, but shares a number of biological activities with the type I interferons.

In humans, at least 16 non-allelic genes code for different subtypes of interferon-α, while interferons β and ω are encoded by single genes. Type I interferon genes are clustered in the short arm of chromosome 9. Unlike typical structural human genes, interferon-α, interferon-β, and interferon-ω lack introns. A single gene for human interferon-γ is localized on chromosome 12 and contains three introns. To date, interferon-τ has been described only in cattle and sheep, while interferon-δ has been described only in pigs.

Clinicians are taking advantage of the multiple activities of interferons by using the proteins to treat a wide range of conditions. For example, one form of interferon-α has been approved for use in more than 50 countries for the treatment of medical conditions such as hairy cell leukemia, renal cell carcinoma, basal cell carcinoma, malignant melanoma, AIDS-related Kaposi's sarcoma, multiple myeloma, chronic myelogenous leukemia, non-Hodgkin's lymphoma, laryngeal papillomatosis, mycosis fungoides, condyloma acuminata, chronic hepatitis B, hepatitis C, chronic hepatitis D, and chronic non-A, non-B/C hepatitis. The U.S. Food and Drug Administration has approved the use of interferon-β to treat multiple sclerosis, a chronic disease of the nervous system. Interferon-γ is used to treat chronic granulomatous diseases, in which the interferon enhances the patient's immune response to destroy infectious bacterial, fungal, and protozoal pathogens. Clinical studies also indicate that interferon-γ may be useful in the treatment of AIDS, leishmaniasis, and lepromatous leprosy.

The demonstrated in vivo activities of the cytokine family illustrate the enormous clinical potential of, and need for, other cytokines, cytokine agonists, and cytokine antagonists. The present invention addresses these needs by providing a new cytokine that stimulates cells of the hematopoietic cell lineage, as well as related compositions and methods.

BRIEF DESCRIPTION OF THE FIGURES

The FIGURE is a Hopp/Woods hydrophilicity profile of the ZZcyto21 protein sequence shown in SEQ ID NO:2. The profile is based on a sliding six-residue window. Buried G, S, and T residues and exposed H, Y, and W residues were ignored. These residues are indicated in the FIGURE by lower case letters.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence. For example, the sequence 5' ATG-CACGGG 3' is complementary to 5'CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "neoplastic", when referring to cells, indicates cells undergoing new and abnormal proliferation, particularly in a tissue where in the proliferation is uncontrolled and progressive, resulting in a neoplasm. The neoplastic cells can be either malignant, i.e. invasive and metastatic, or benign.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

Zcyto21 gene encodes a polypeptide of 200 amino acids, as shown in SEQ ID NO:2. The signal sequence for Zcyto21 can be predicted as comprising amino acid residue 1 (Met) through amino acid residue 19 (Ala) of SEQ ID NO:2. The mature peptide for Zcyto21 begins at amino acid residue 20 (Gly).

The Zcyto21 gene is contained in BAC sequences AC011445, and AC018477 which have been mapped to human chromosome 19q13.13. This region of chromosome 19 may also comprise a cluster of interferon-like genes. A consensus cDNA showing a polynucleotide sequence of Zcyto21 is shown in SEQ ID NO:6 and the polypeptide it encodes is shown in SEQ ID NO:7.

As described below, the present invention provides isolated polypeptides having an amino acid sequence that is at least 70%, at least 80%, or at least 90%, 95%, 96%, 97%, 98% or 99% identical to either amino acid residues 20 to 200 of SEQ ID NO:2 or amino acid residues 1 to 200 of SEQ ID NO:2. The present invention also provides isolated polypeptides having an amino acid sequence that is at least 70%, at least 80%, or at least 90%, 95%, 96%, 97%, 98% or 99% identical to either amino acid residues 20 to 219 of SEQ ID NO:9 or amino acid residues 1 to 219 of SEQ ID NO:9. The present invention also provides isolated polypeptides having an amino acid sequence that is at least 70%, at least 80%, or at least 90%, 95%, 96%, 97%, 98% or 99% identical to either amino acid residues 20 to 203 of SEQ ID NO:12 or amino acid residues 1 to 203 of SEQ ID NO:12. The present invention also includes a polypeptide that further comprises a signal secretory sequence that resides in an amino-terminal position relative to the first amino acid sequence, wherein the signal secretory sequence comprises amino acid residues 1 to 19 of the amino acid sequence of SEQ ID NO:2.

In general, cytokines are predicted to have a four-alpha helix structure, with helices A, C and D being most important in ligand-receptor interactions, and are more highly conserved among members of the family. However, the interferons (INF), and interferon-alpha and interferon-tau in particular, are characterized as six helix bundles. INF helix A is equivalent to helix A of Zcyto21; INF helix B is equivalent to helix C of Zcyto21; INF helix C is equivalent to helix D of Zcyto21, and INF helix D is equivalent to helix F of Zcyto21. Thus, the loop between the AB loop, and CD loop of INF is expanded in Zcyto21 to contain short helices B and E of Zcyto21.

Zcyto21 helices are predicted as follows: helix A is defined by amino acid residues 49 (Ser) to 63 (Leu); helix B by amino acid residues 76 (Asn) to 84(Val); helix C by amino acid residues 89 (Val) to 104 (Ala); helix D by amino acid residues 111 (Glu) to 133 (Gln); helix E by amino acid residues 137 (Thr) to 158 (Lys); and helix F by amino acid residues 163 (Gly) to 189 (Leu); as shown in SEQ ID NO: 2. The cysteine residues are conserved between Zcyto21, and INF-α, and may form an intermolecular disulfide bond, in particular to form homodimers with additional Zcyto21 molecules. Further analysis of Zcyto21 based on multiple alignments predicts that cysteines at amino acid residues 34 and 131, and 68 and 164, (as shown in SEQ ID NO: 2) will form intramolecular disulfide bonds. The cysteine at residue 190 is free, and may form an intermolecular disulfide association. The corresponding polynucleotides encoding the Zcyto21 polypeptide regions, domains, motifs, residues and sequences described herein are as shown in SEQ ID NO:1. The degenerate polynucleotide sequence of SEQ ID NO:2 is shown in SEQ ID NO:3. The degenerate polynucleotide sequence of SEQ ID NO:9 is shown in SEQ ID NO:10. The degenerate polynucleotide sequence of SEQ ID NO:12 is shown in SEQ ID NO:13.

Detailed mutational analysis of murine IL-2 (Zurawski et al., *EMBO J.* 12:5113-5119, 1993) shows residues in helices A and C are important for binding to IL-2Rβ; critical residues are $Asp_{34}$, $Asn_{99}$, and $Asn_{103}$. Multiple residues within murine IL-2 loop A/B and helix B are important for IL-2Rα binding, while only a single residue, $Gin_{141}$ in helix D, is vital for binding with IL-2Rα. Similarly, helices A and C are sites of interaction between IL-4 and IL-4Rα (the structurally similar to IL-2Rα), and residues within helix D are vital for IL-2Rα interaction (Wang et al., *Proc. Natl. Acad. Sci. USA* 94:1657-1662, 1997; Kruse et al., *EMBO J.* 11:3237-3244, 1992). In particular, the mutation $Tyr_{124}$ to Asp in human IL-4 creates an antagonist, which binds with IL-4Rα but not IL-2Rα and therefore cannot signal (Kruse et al. ibid. 1992).

Four-helical bundle cytokines are also grouped by the length of their component helices. "Long-helix" form cytokines generally consist of between 24-30 residue helices, and include IL-6, ciliary neutrotrophic factor (CNTF), leukemia inhibitory factor (LIF) and human growth hormone (hGH). "Short-helix" form cytokines generally consist of between 18-21 residue helices and include IL-2, IL-4 and GM-CSF. Studies using CNTF and IL-6 demonstrated that a CNTF helix can be exchanged for the equivalent helix in IL-6, conferring CTNF-binding properties to the chimera. Thus, it appears that functional domains of four-helical cytokines are determined on the basis of structural homology, irrespective of sequence identity, and can maintain functional integrity in a chimera (Kallen et al., *J. Biol. Chem.* 274:11859-11867, 1999). Therefore, the helical domains of Zcyto21 will be useful for preparing chimeric fusion molecules, particularly with other interferons to determine and modulate receptor binding specificity. Of particular interest are fusion proteins that combine helical and loop domains from interferons and cytokines such as INF-α, IL-10, human growth hormone.

Zcyto21 mRNA has been identified in tissues of brain, islet, prostate, testis, pituitary, placenta, ovarian tumor, lung tumor, rectal tumor and ovarian tumor, as well as an activated immune cell line (CD3+) and a prostate epithelial cell line, which had been transformed with human papilloma virus IV (HPVS).

The present invention provides polynucleotide molecules, including DNA and RNA molecules, that encode the Zcyto21 polypeptides disclosed herein. Those skilled in the art will readily recognize that, in view of the degeneracy of the genetic code, considerable sequence variation is possible among these polynucleotide molecules. SEQ ID NOs:3, 10, and 13 are degenerate DNA sequences that encompasses all DNAs that encode the Zcyto21 polypeptide of SEQ ID NOs:2, 9, and 12, respectively. Those skilled in the art will recognize that the degenerate sequence of SEQ ID NO:3, for example, also provides all RNA sequences encoding SEQ ID NO:2 by substituting U for T. Thus, Zcyto21 polypeptide-encoding polynucleotides comprising nucleotide 1 or 58 to nucleotide 603 of SEQ ID NO:3 and their RNA equivalents are contemplated by the present invention. Table 1 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, with A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs:3, 10, and 13, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |

TABLE 2-continued

| Amino Acid | One Letter Code | Codons | Degenerate Codon |
|---|---|---|---|
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893-912, 1980; Haas, et al. *Curr. Biol.* 6:315-24, 1996; Wain-Hobson, et al., *Gene* 13:355-64, 1981; Grosjean and Fiers, *Gene* 18:199-209, 1982; Holm, *Nuc. Acids Res.* 14:3075-87, 1986; Ikemura, *J. Mol. Biol.* 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 3). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

As previously noted, the isolated polynucleotides of the present invention include DNA and RNA. Methods for preparing DNA and RNA are well known in the art. In general, RNA is isolated from a tissue or cell that produces large amounts of Zcyto21 RNA. Such tissues and cells are identified by Northern blotting (Thomas, *Proc. Natl. Acad. Sci. USA* 77:5201, 1980), or by screening conditioned medium from various cell types for activity on target cells or tissue. Once the activity or RNA producing cell or tissue is identified, total RNA can be prepared using guanidinium isothiocyanate extraction followed by isolation by centrifugation in a CsCl gradient (Chirgwin et al., *Biochemistry* 18:52-94, 1979). Poly (A)$^+$ RNA is prepared from total RNA using the method of Aviv and Leder (*Proc. Natl. Acad. Sci. USA* 69:1408-12, 1972). Complementary DNA (cDNA) is prepared from poly(A)$^+$ RNA using known methods. In the alternative, genomic DNA can be isolated. Polynucleotides encoding Zcyto21 polypeptides are then identified and isolated by, for example, hybridization or PCR.

A longer clone encoding Zcyto21 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to Zcyto21 receptor fragments, or other specific binding partners.

The present invention further provides counterpart polypeptides and polynucleotides from other species (orthologs). These species include, but are not limited to mammalian, avian, amphibian, reptile, fish, insect and other vertebrate and invertebrate species. Of particular interest are Zcyto21 polypeptides from other mammalian species, including murine, porcine, ovine, bovine, canine, feline, equine, and other primate polypeptides. Orthologs of human Zcyto21 can be cloned using information and compositions provided by the present invention in combination with conventional cloning techniques. For example, a cDNA can be cloned using mRNA obtained from a tissue or cell type that expresses Zcyto21 as disclosed herein. Suitable sources of mRNA can be identified by probing Northern blots with probes designed from the sequences disclosed herein. A library is then prepared from mRNA of a positive tissue or cell line. A Zcyto21-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human Zcyto21 sequence disclosed herein. Within an additional method, the cDNA library can be used to transform or transfect host cells, and expression of the cDNA of interest can be detected with an antibody to Zcyto21 polypeptide, binding studies or activity assays. Similar techniques can also be applied to the isolation of genomic clones.

Those skilled in the art will recognize that the sequence disclosed in SEQ ID NO:1 represents a single allele of human Zcyto21 band that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the Zcyto21 polypeptide, are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art. Examples of alternatively spliced variants are shown in SEQ ID NO:8 (SEQ ID NO:9 for the corresponding polypeptide), and in SEQ ID NO:11 (SEQ ID NO:12 for the corresponding polypeptide). An example of an allelic variant is shown in SEQ ID NO:4, which corresponds to the polypeptide sequence as shown in SEQ ID NO:5. There is a polymorphism between the polypeptide sequence as shown in SEQ ID NO:1 and that shown in SEQ ID NO:4 at nucleotide number 572. This polymorphism might create an antagonist of Zcyto21 or a molecule of reduced or altered function, which might lead to a higher likelihood of disease susceptibility.

The present invention also provides reagents, which will find use in diagnostic applications. For example, the Zcyto21 gene, a probe comprising Zcyto21 DNA or RNA or a subsequence thereof can be used to determine if the Zcyto21 gene is present on a human chromosome, such as chromosome 19, or if a gene mutation has occurred. Zcyto21 is located at the q13.13 region of chromosome 19. Detectable chromosomal aberrations at the Zcyto21 gene locus include, but are not limited to, aneuploidy, gene copy number changes, loss of heterogeneity (LOH), translocations, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid; Ausubel et. al., ibid.; Marian, *Chest* 108:255-65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

For example, Delague et al., (Am. J. Hum. Genet. 67: 236-243, 2000) identified that Charcot-Marie-Tooth disease is localized to 19q13.1-13.3 (Delague et al., Am. J. Hum. Genet. 67: 236-243, 2000).

A diagnostic could assist physicians in determining the type of disease and appropriate associated therapy, or assistance in genetic counseling. As such, the inventive anti-Zcyto21 antibodies, polynucleotides, and polypeptides can be used for the detection of Zcyto21 polypeptide, mRNA or anti-Zcyto21 antibodies, thus serving as markers and can be directly used for detecting or genetic diseases or cancers, as described herein, using methods known in the art and described herein. Further, Zcyto21 polynucleotide probes can be used to detect abnormalities or genotypes associated with chromosome 19 deletions and translocations associated with human diseases or other translocations involved with malignant progression of tumors or other 19q13.13 mutations, which are expected to be involved in chromosome rearrangements in malignancy; or in other cancers. Similarly, Zcyto21 polynucleotide probes can be used to detect abnormalities or genotypes associated with chromosome 19q13.13 trisomy and chromosome loss associated with human diseases or spontaneous abortion. Thus, Zcyto21 polynucleotide probes can be used to detect abnormalities or genotypes associated with these defects.

In general, the diagnostic methods used in genetic linkage analysis, to detect a genetic abnormality or aberration in a patient, are known in the art. Analytical probes will be generally at least 20 nt in length, although somewhat shorter probes can be used (e.g., 14-17 nt). PCR primers are at least 5 nt in length, preferably 15 or more, more preferably 20-30 nt. For gross analysis of genes, or chromosomal DNA, a Zcyto21 polynucleotide probe may comprise an entire exon or more. Exons are readily determined by one of skill in the art by comparing Zcyto21 sequences (SEQ ID NO:1) with the genomic DNA for Zcyto21. In general, the diagnostic methods used in genetic linkage analysis, to detect a genetic abnormality or aberration in a patient, are known in the art. Most diagnostic methods comprise the steps of (a) obtaining a genetic sample from a potentially diseased patient, diseased patient or potential non-diseased carrier of a recessive disease allele; (b) producing a first reaction product by incubating the genetic sample with a Zcyto21 polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) Visualizing the first reaction product by gel electrophoresis and/or other known method such as visualizing the first reaction product with a Zcyto21 polynucleotide probe wherein the polynucleotide will hybridize to the complementary polynucleotide sequence of the first reaction; and (iv) comparing the visualized first reaction product to a second control reaction product of a genetic sample from wild type patient. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the Zcyto21 genetic locus, and the like, are indicative of a genetic abnormality, genetic aberration, or allelic difference in comparison to the normal wild type control. Controls can be from unaffected family members, or unrelated individuals, depending on the test and availability of samples. Genetic samples for use within the present invention include genomic DNA, mRNA, and cDNA isolated form any tissue or other biological sample from a patient, such as but not limited to, blood, saliva, semen, embryonic cells, amniotic fluid, and the like. The polynucleotide probe or primer can be RNA or DNA, and will comprise a portion of SEQ ID NO:1, the complement of SEQ ID NO:1, or an RNA equivalent thereof. Such methods of showing genetic linkage analysis to human disease phenotypes are well known in the art. For reference to PCR based methods in diagnostics see see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Mutations associated with the Zcyto21 locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83-88 (Humana Press, Inc. 1998)). Direct analysis of an Zcyto21 gene for a mutation can be performed using a subject's genomic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

Within embodiments of the invention, isolated Zcyto21-encoding nucleic acid molecules can hybridize under stringent conditions to nucleic acid molecules having the nucleotide sequence of SEQ ID NO:1, to nucleic acid molecules having the nucleotide sequence of nucleotides 58 to 603 of SEQ ID NO:1, or to nucleic acid molecules having a nucleotide sequence complementary to SEQ ID NO:1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases.

It is well within the abilities of one skilled in the art to adapt these conditions for use with a particular polynucleotide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Clon-* ing: *A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated $T_m$. For smaller probes, <50 base pairs, hybridization is typically carried out at the $T_m$ or 5-10° C. below the calculated $T_m$. This allows for the maximum rate of hybridization for DNA-DNA and DNA-RNA hybrids.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. That is, nucleic acid molecules encoding a variant Zcyto21 polypeptide hybridize with a nucleic acid molecule having the nucleotide sequence of SEQ ID NO:1 (or its complement) under stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. In other words, nucleic acid molecules encoding a variant Zcyto21 polypeptide hybridize with a nucleic acid molecule having the nucleotide sequence of SEQ ID NO:1 (or its complement) under highly stringent washing conditions, in which the wash stringency is equivalent to 0.1×-0.2×SSC with 0.1% SDS at 50-65° C., including 0.1×SSC with 0.1% SDS at 50° C., or 0.2×SSC with 0.1% SDS at 65° C.

The present invention also provides isolated Zcyto21 polypeptides that have a substantially similar sequence identity to the polypeptides of SEQ ID NO:2, or their orthologs. The term "substantially similar sequence identity" is used herein to denote polypeptides comprising at least 70%, at least 80%, at least 90%, at least 95%, or greater than 95%, 96%, 97%, 98%, or 99% sequence identity to the sequences shown in SEQ ID NO:2, or their orthologs. The present invention also includes polypeptides that comprise an amino acid sequence having at least 70%, at least 80%, at least 90%, at least 95% or greater than 95%, 96%, 97%, 98%, or 99% sequence identity to the sequence of amino acid residues 1 to 200 or 20 to 200 of SEQ ID NO:2. The present invention further includes nucleic acid molecules that encode such polypeptides. Methods for determining percent identity are described below.

The present invention also contemplates variant Zcyto21 nucleic acid molecules that can be identified using two criteria: a determination of the similarity between the encoded polypeptide with the amino acid sequence of SEQ ID NO:2, and/or a hybridization assay, as described above. Such Zcyto21 variants include nucleic acid molecules: (1) that hybridize with a nucleic acid molecule having the nucleotide sequence of SEQ ID NO:1 (or its complement) under stringent washing conditions, in which the wash stringency is equivalent to 0.5×-2×SSC with 0.1% SDS at 55-65° C.; or (2) that encode a polypeptide having at least 70%, at least 80%, at least 90%, at least 95% or greater than 95%, 96%, 97%, 98%, or 99% sequence identity to the amino acid sequence of SEQ ID NO:2. Alternatively, Zcyto21 variants can be characterized as nucleic acid molecules: (1) that hybridize with a nucleic acid molecule having the nucleotide sequence of SEQ ID NO:1 (or its complement) under highly stringent washing conditions, in which the wash stringency is equivalent to 0.1×-0.2×SSC with 0.1% SDS at 50-65° C.; and (2) that encode a polypeptide having at least 70%, at least 80%, at least 90%, at least 95% or greater than 95% sequence identity to the amino acid sequence of SEQ ID NO:2.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes).

$$\frac{\text{Total number of identical matches}}{[\text{length of the longer sequence plus the number of gaps introduced into the longer sequence in order to align the two sequences}]} \times 100$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |

TABLE 3-continued

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | 2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant Zcyto21. The FASTA algorithm is described by Pearson and Lipman, Proc. Nat'l Acad. Sci. USA 85:2444 (1988), and by Pearson, Meth. Enzymol. 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variant Zcyto21 polypeptides or polypeptides with substantially similar sequence identity are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20-25 residues, or an affinity tag. The present invention thus includes polypeptides of from about 149 to 230 amino acid residues that comprise a sequence that is at least 70%, preferably at least 90%, and more preferably 95%, 96%, 97%, 98%, 99% or more identical to the corresponding region of SEQ ID NO:2. Polypeptides comprising affinity tags can further comprise a proteolytic cleavage site between the Zcyto21 polypeptide and the affinity tag. Preferred such sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |

TABLE 4-continued

Conservative amino acid substitutions

| | |
|---|---|
| Small: | glycine |
| | alanine |
| | serine |
| | threonine |
| | methionine |

Determination of amino acid residues that comprise regions or domains that are critical to maintaining structural integrity can be determined. Within these regions one can determine specific residues that will be more or less tolerant of change and maintain the overall tertiary structure of the molecule. Methods for analyzing sequence structure include, but are not limited to alignment of multiple sequences with high amino acid or nucleotide identity, secondary structure propensities, binary patterns, complementary packing and buried polar interactions (Barton, Current Opin. Struct. Biol. 5:372-376, 1995 and Cordes et al., Current Opin. Struct. Biol. 6:3-10, 1996). In general, when designing modifications to molecules or identifying specific fragments determination of structure will be accompanied by evaluating activity of modified molecules.

Amino acid sequence changes are made in Zcyto21 polypeptides so as to minimize disruption of higher order structure essential to biological activity. For example, where the Zcyto21 polypeptide comprises one or more helices, changes in amino acid residues will be made so as not to disrupt the helix geometry and other components of the molecule where changes in conformation abate some critical function, for example, binding of the molecule to its binding partners. The effects of amino acid sequence changes can be predicted by, for example, computer modeling as disclosed above or determined by analysis of crystal structure (see, e.g., Lapthorn et al., *Nat. Struct. Biol.* 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same cysteine pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structurally similarities between proteins and polypeptides (Schaanan et al., *Science* 257:961-964, 1992).

A Hopp/Woods hydrophilicity profile of the Zcyto21 protein sequence as shown in SEQ ID NO:2 can be generated (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. For example, in Zcyto21, hydrophilic regions include residues 155 (Glu) to 160 (Glu); residues 51 (Lys) to 56 (Ala); residues 50 (Phe) to 55 (Asp); residues 140 (Pro) to 145 (Arg); and residues 154 (Gln) to 159 (Lys); as shown in SEQ ID NO: 2.

Those skilled in the art will recognize that hydrophilicity or hydrophobicity will be taken into account when designing modifications in the amino acid sequence of a Zcyto21 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp.

The identities of essential amino acids can also be inferred from analysis of sequence similarity between INF-α and other interferons. Using methods such as "FASTA" analysis described previously, regions of high similarity are identified within a family of proteins and used to analyze amino acid sequence for conserved regions. An alternative approach to identifying a variant Zcyto21 polynucleotide on the basis of structure is to determine whether a nucleic acid molecule encoding a potential variant Zcyto21 gene can hybridize to a nucleic acid molecule having the nucleotide sequence of SEQ ID NO:1, as discussed above.

Other methods of identifying essential amino acids in the polypeptides of the present invention are procedures known in the art, such as site-directed mutagenesis or alanine-scanning mutagenesis (Cunningham and Wells, *Science* 244: 1081 (1989), Bass et al., *Proc. Natl. Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological or biochemical activity as disclosed below to identify amino acid residues that are critical to the activity of the molecule. See also, Hilton et al., *J. Biol. Chem.* 271:4699 (1996).

The present invention also includes functional fragments of Zcyto21 polypeptides and nucleic acid molecules encoding such functional fragments. A "functional" Zcyto21 or fragment thereof as defined herein is characterized by its proliferative or differentiating activity, by its ability to induce or inhibit specialized cell functions, or by its ability to bind specifically to an anti-Zcyto21 antibody or Zcyto21 receptor (either soluble or immobilized). As previously described herein, Zcyto21 is characterized by a six-helical-bundle structure comprising: helix A is defined by amino acid residues 49 (Ser) to 63 (Leu); helix B by amino acid residues 76 (Asn) to 84 (Val); helix C by amino acid residues 89 (Val) to 104 (Ala); helix D by amino acid residues 111 (Glu) to 133 (Gln); helix E by amino acid residues 137 (Thr) to 158 (Lys); and helix F by amino acid residues 163 (Gly) to 189 (Leu); as shown in SEQ ID NO: 2. Thus, the present invention further provides fusion proteins encompassing: (a) polypeptide molecules comprising one or more of the helices described above; and (b) functional fragments comprising one or more of these helices. The other polypeptide portion of the fusion protein may be contributed by another helical-bundle cytokine or interferon, such as INF-α, or by a non-native and/or an unrelated secretory signal peptide that facilitates secretion of the fusion protein.

The Zcyto21 polypeptides of the present invention, including full-length polypeptides, biologically active fragments, and fusion polypeptides can be produced according to conventional techniques using cells into which have been introduced an expression vector encoding the polypeptide.

As used herein, "cells into which have been introduced an expression vector" include both cells that have been directly manipulated by the introduction of exogenous DNA molecules and progeny thereof that contain the introduced DNA. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a Zcyto21 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Zcyto21 polypeptide into the secretory pathway of a host cell, a secretory signal sequence (also known as a leader sequence, prepro sequence or pre sequence) is provided in the expression vector. The secretory signal sequence may be that of Zcyto21, or may be derived from another secreted protein (e.g., t-PA; see, U.S. Pat. No. 5,641,655) or synthesized de novo. The secretory signal sequence is operably linked to the Zcyto21 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells can be used as hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1, ATCC No. CCL 61; or CHO DG44, Chasin et al., *Som. Cell. Molec. Genet.* 12:555, 1986) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter. Expression vectors for use in mammalian cells include pZP-1 and pZP-9, which have been deposited with the American Type Culture Collection, Manassas, Va. USA under accession numbers 98669 and 98668, respectively, and derivatives thereof.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. In an alternative method, adenovirus vector-infected 293 cells can be grown as adherent cells or in suspension culture at relatively high cell density to produce significant amounts of protein (See Garnier et al., *Cytotechnol.* 15:145-55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins can also be effectively obtained.

Insect cells can be infected with recombinant baculovirus, commonly derived from *Autographa californica* nuclear polyhedrosis virus (AcNPV) according to methods known in the art. Within a preferred method, recombinant baculovirus is produced through the use of a transposon-based system described by Luckow et al. (*J. Virol.* 67:4566-4579, 1993). This system, which utilizes transfer vectors, is commercially available in kit form (Bac-to-Bac™ kit; Life Technologies, Rockville, Md.). The transfer vector (e.g., pFastBac1™; Life Technologies) contains a Tn7 transposon to move the DNA encoding the protein of interest into a baculovirus genome maintained in *E. coli* as a large plasmid called a "bacmid." See, Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a Zcyto21-encoding sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses Zcyto21 protein is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., High Five™ cells; Invitrogen, Carlsbad, Calif.). See, for example, U.S. Pat. No. 5,300,435. Serum-free media are used to grow and maintain the cells. Suitable media formulations are known in the art and can be obtained from commercial suppliers. The cells are grown up from an inoculation density of approximately 2-5×$10^5$ cells to a density of 1-2×$10^6$ cells, at which time a recombinant viral stock is added at a multiplicity of infection (MOI) of 0.1 to 10, more typically near 3. Procedures used are generally known in the art.

Other higher eukaryotic cells can also be used as hosts, including plant cells and avian cells. The use of *Agrobacterium rhizogenes* as a vector for expressing genes in plant cells has been reviewed by Sinkar et al., *J. Biosci.* (*Bangalore*) 11:47-58, 1987.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POTI vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459-3465, 1986; Cregg, U.S. Pat. No. 4,882,279; and Raymond et al., *Yeast* 14, 11-23, 1998. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808, 5,736,383, 5,854,039, and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a Zcyto21 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. Liquid cultures are provided with sufficient aeration by conventional means, such as shaking of small flasks or sparging of fermentors.

It is preferred to purify the polypeptides and proteins of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide or protein is substantially free of other polypeptides or proteins, particularly those of animal origin.

Expressed recombinant Zcyto21 proteins (including chimeric polypeptides and multimeric proteins) are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321-1325, 1988. Proteins comprising a glu-glu tag can be purified by immunoaffinity chromatography according to conventional procedures. See, for example, Grussenmeyer et al., ibid. Maltose binding protein fusions are purified on an amylose column according to methods known in the art.

Zcyto21 polypeptides can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989. In vitro synthesis is particularly advantageous for the preparation of smaller polypeptides.

Using methods known in the art, Zcyto21 proteins can be prepared as monomers or multimers; glycosylated or non-glycosylated; pegylated or non-pegylated; and may or may not include an initial methionine amino acid residue.

Target cells for use in Zcyto21 activity assays include, without limitation, vascular cells (especially endothelial cells and smooth muscle cells), hematopoietic (myeloid and lymphoid) cells, liver cells (including hepatocytes, fenestrated endothelial cells, Kupffer cells, and Ito cells), fibroblasts (including human dermal fibroblasts and lung fibroblasts), fetal lung cells, articular synoviocytes, pericytes, chondrocytes, osteoblasts, and prostate epithelial cells. Endothelial cells and hematopoietic cells are derived from a common ancestral cell, the hemangioblast (Choi et al., *Development* 125:725-732, 1998).

Zcyto21 proteins of the present invention are characterized by their activity, that is, modulation of the proliferation, differentiation, migration, adhesion, or metabolism of responsive cell types. Biological activity of Zcyto21 proteins is assayed using in vitro or in vivo assays designed to detect cell proliferation, differentiation, migration or adhesion; or changes in cellular metabolism (e.g., production of other growth factors or other macromolecules). Many suitable assays are known in the art, and representative assays are disclosed herein. Assays using cultured cells are most convenient for screening, such as for determining the effects of amino acid substitutions, deletions, or insertions. However, in view of the complexity of developmental processes (e.g., angiogenesis, wound healing), in vivo assays will generally be employed to confirm and further characterize biological activity. Certain in vitro models, such as the three-dimensional collagen gel matrix model of Pepper et al. (*Biochem. Biophys. Res. Comm.* 189:824-831, 1992), are sufficiently complex to assay histological effects. Assays can be performed using exogenously produced proteins, or may be carried out in vivo or in vitro using cells expressing the polypeptide(s) of interest. Assays can be conducted using Zcyto21 proteins alone or in combination with other growth factors, such as members of the VEGF family or hematopoietic cytokines (e.g., EPO, TPO, G-CSF, stem cell factor). Representative assays are disclosed below.

Activity of Zcyto21 proteins can be measured in vitro using cultured cells or in vivo by administering molecules of the claimed invention to an appropriate animal model. Assays measuring cell proliferation or differentiation are well known in the art. For example, assays measuring proliferation include such assays as chemosensitivity to neutral red dye (Cavanaugh et al., *Investigational New Drugs* 8:347-354, 1990), incorporation of radiolabelled nucleotides (as disclosed by, e.g., Raines and Ross, *Methods Enzymol.* 109:749-773, 1985; Wahl et al., *Mol. Cell Biol.* 8:5016-5025, 1988; and Cook et al., *Analytical Biochem.* 179:1-7, 1989), incorporation of 5-bromo-2'-deoxyuridine (BrdU) in the DNA of proliferating cells (Porstmann et al., *J. Immunol. Methods* 82:169-179, 1985), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988). Differentiation can be assayed using suitable precursor cells that can be induced to differentiate into a more mature phenotype. Assays measuring differentiation include, for example, measuring cell-surface markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol. Bioprocesses*, 161-171, 1989; all incorporated herein by reference).

Zcyto21 activity may also be detected using assays designed to measure Zcyto21-induced production of one or more additional growth factors or other macromolecules. Preferred such assays include those for determining the presence of hepatocyte growth factor (HGF), epidermal growth factor (EGF), transforming growth factor alpha (TGFα), interleukin-6 (IL-6), VEGF, acidic fibroblast growth factor (aFGF), angiogenin, and other macromolecules produced by the liver. Suitable assays include mitogenesis assays using target cells responsive to the macromolecule of interest, receptor-binding assays, competition binding assays, immunological assays (e.g., ELISA), and other formats known in the art. Metalloprotease secretion is measured from treated primary human dermal fibroblasts, synoviocytes and chondrocytes. The relative levels of collagenase, gelatinase and stromalysin produced in response to culturing in the presence of a Zcyto21 protein is measured using zymogram gels (Loita and Stetler-Stevenson, *Cancer Biology* 1:96-106, 1990). Procollagen/collagen synthesis by dermal fibroblasts and chondrocytes in response to a test protein is measured using $^3$H-proline incorporation into nascent secreted collagen. $^3$H-labeled collagen is visualized by SDS-PAGE followed by autoradiography (Unemori and Amento, *J. Biol. Chem.* 265: 10681-10685, 1990). Glycosaminoglycan (GAG) secretion from dermal fibroblasts and chondrocytes is measured using a 1,9-dimethylmethylene blue dye binding assay (Farndale et al., *Biochim. Biophys. Acta* 883:173-177, 1986). Collagen and GAG assays are also carried out in the presence of IL-1α or TGF-α to examine the ability of Zcyto21 protein to modify the established responses to these cytokines.

Monocyte activation assays are carried out (1) to look for the ability of Zcyto21 proteins to further stimulate monocyte activation, and (2) to examine the ability of Zcyto21 proteins to modulate attachment-induced or endotoxin-induced monocyte activation (Fuhlbrigge et al., *J. Immunol.* 138: 3799-3802, 1987). IL-1α and TNFα levels produced in response to activation are measured by ELISA (Biosource, Inc. Camarillo, Calif.). Monocyte/macrophage cells, by virtue of CD14 (LPS receptor), are exquisitely sensitive to endotoxin, and proteins with moderate levels of endotoxin-like activity will activate these cells.

Hematopoietic activity of Zcyto21 proteins can be assayed on various hematopoietic cells in culture. Preferred assays include primary bone marrow colony assays and later stage lineage-restricted colony assays, which are known in the art (e.g., Holly et al., WIPO Publication WO 95/21920). Marrow cells plated on a suitable semi-solid medium (e.g., 50% methylcellulose containing 15% fetal bovine serum, 10% bovine serum albumin, and 0.6% PSN antibiotic mix) are incubated in the presence of test polypeptide, then examined microscopically for colony formation. Known hematopoietic factors are used as controls. Mitogenic activity of Zcyto21 polypeptides on hematopoietic cell lines can be measured as disclosed above.

Cell migration is assayed essentially as disclosed by Kähler et al. (*Arteriosclerosis, Thrombosis, and Vascular Biology* 17:932-939, 1997). A protein is considered to be chemotactic if it induces migration of cells from an area of low protein concentration to an area of high protein concentration. A typical assay is performed using modified Boyden chambers with a polystryrene membrane separating the two chambers (Transwell; Corning Costar Corp.). The test sample, diluted in medium containing 1% BSA, is added to the lower chamber of a 24-well plate containing Transwells. Cells are then placed on the Transwell insert that has been pretreated with 0.2% gelatin. Cell migration is measured after 4 hours of incubation at 37° C. Non-migrating cells are wiped off the top of the Transwell membrane, and cells attached to the lower face of the membrane are fixed and stained with 0.1% crystal violet. Stained cells are then extracted with 10% acetic acid and absorbance is measured at 600 nm. Migration is then calculated from a standard calibration curve. Cell migration can also be measured using the matrigel method of Grant et al. ("Angiogenesis as a component of epithelial-mesenchymal interactions" in Goldberg and Rosen, *Epithelial-Mesenchymal Interaction in Cancer*, Birkhäuser Verlag, 1995, 235-248; Baatout, *Anticancer Research* 17:451-456, 1997).

Cell adhesion activity is assayed essentially as disclosed by LaFleur et al. (*J. Biol. Chem.* 272:32798-32803, 1997). Briefly, microtiter plates are coated with the test protein, non-specific sites are blocked with BSA, and cells (such as smooth muscle cells, leukocytes, or endothelial cells) are plated at a density of approximately $10^4$-$10^5$ cells/well. The wells are incubated at 37° C. (typically for about 60 minutes), then non-adherent cells are removed by gentle washing. Adhered cells are quantitated by conventional methods (e.g., by staining with crystal violet, lysing the cells, and determining the optical density of the lysate). Control wells are coated with a known adhesive protein, such as fibronectin or vitronectin.

The activity of Zcyto21 proteins can be measured with a silicon-based biosensor microphysiometer that measures the extracellular acidification rate or proton excretion associated with receptor binding and subsequent physiologic cellular responses. An exemplary such device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell et al., *Science* 257:1906-1912, 1992; Pitchford et al., *Meth. Enzymol.* 228:84-108, 1997; Arimilli et al., *J. Immunol. Meth.* 212:49-59, 1998; and Van Liefde et al., *Eur. J. Pharmacol.* 346:87-95, 1998. The microphysiometer can be used for assaying adherent or non-adherent eukaryotic or prokaryotic cells. By measuring extracellular acidification changes in cell media over time, the microphysiometer directly measures cellular responses to various stimuli, including Zcyto21 proteins, their agonists, and antagonists. Preferably, the microphysiometer is used to measure responses of a Zcyto21-responsive eukaryotic cell, compared to a control eukaryotic cell that does not respond to Zcyto21 polypeptide. Zcyto21-responsive eukaryotic cells comprise cells into which a receptor for Zcyto21 has been transfected, thereby creating a cell that is responsive to Zcyto21, as well as cells naturally responsive to Zcyto21. Differences, measured by a change, for example, an increase or diminution in extracellular acidification, in the response of cells exposed to Zcyto21 polypeptide, relative to a control not exposed to Zcyto21, are a direct measurement of Zcyto21-modulated cellular responses. Moreover, such Zcyto21-modulated responses can be assayed under a variety of stimuli. The present invention thus provides methods of identifying agonists and antagonists of Zcyto21 proteins, comprising providing cells responsive to a Zcyto21 polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change in extracellular acidification rate. Culturing a third portion of the cells in the presence of a Zcyto21 protein and the absence of a test compound provides a positive control for the Zcyto21-responsive cells and a control to compare the agonist activity of a test compound with that of the Zcyto21 polypeptide. Antagonists of Zcyto21 can be identified by exposing the cells to Zcyto21 protein in the presence and absence of the test compound, whereby a reduction in Zcyto21-stimulated activity is indicative of antagonist activity in the test compound.

Expression of Zcyto21 polynucleotides in animals provides models for further study of the biological effects of overproduction or inhibition of protein activity in vivo. Zcyto21-encoding polynucleotides and antisense polynucleotides can be introduced into test animals, such as mice, using viral vectors or naked DNA, or transgenic animals can be produced.

One in vivo approach for assaying proteins of the present invention utilizes viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161-89, 1994; and Douglas and Curiel, *Science & Medicine* 4:44-53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene is deleted from the viral vector, and the virus will not replicate unless the E1 gene is provided by the host cell (e.g., the human 293 cell line). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein. Secreted proteins will enter the circulation in the highly vascularized liver, and effects on the infected animal can be determined.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., *J. Biol. Chem.* 263:14621-14624, 1988; Wu et al., *J. Biol. Chem.* 267:963-967, 1992; and Johnston and Tang, *Meth. Cell Biol.* 43:353-365, 1994.

Transgenic mice, engineered to express a Zcyto21 gene, and mice that exhibit a complete absence of Zcyto21 gene function, referred to as "knockout mice" (Snouwaert et al., *Science* 257:1083, 1992), can also be generated (Lowell et al., *Nature* 366:740-742, 1993). These mice can be employed to study the Zcyto21 gene and the protein encoded thereby in an in vivo system. Transgenic mice are particularly useful for investigating the role of Zcyto21 proteins in early development in that they allow the identification of developmental abnormalities or blocks resulting from the over- or underexpression of a specific factor. See also, Maisonpierre et al., *Science* 277:55-60, 1997 and Hanahan, *Science* 277:48-50, 1997. Preferred promoters for transgenic expression include promoters from metallothionein and albumin genes.

A loss of normal inhibitory control of muscle contraction has been associated with damage or perturbation of selected gamma-aminobutryric acid-secreting neurons. For example, Stiff Man Syndrome exhibit remarkable stiffness of musculature, believed to be mediated through interference of the functioning of their gamma-aminobutryric acid (GABA) producing neurons. Other related neuromuscular disorders include myotonia, metabolic myopathies, Isaac's syndrome, dystonia, and tetanic spasms (Valldeoriola, *J. Neurol* 246: 423-431, 1999).

Similarly, direct measurement of Zcyto21 polypeptide, or its loss of expression in a tissue can be determined in a tissue or cells as they undergo tumor progression. Increases in invasiveness and motility of cells, or the gain or loss of expression of Zcyto21 in a pre-cancerous or cancerous condition, in comparison to normal tissue, can serve as a diagnostic for transformation, invasion and metastasis in tumor progression. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to Zcyto21 expression. For example, appearance or disappearance of polypeptides that regulate cell motility can be used to aid diagnosis and prognosis of prostate cancer (Banyard, J. and Zetter, B. R., *Cancer and Metast. Rev.* 17;449-458, 1999). As an effector of cell motility, or as a liver-specific marker, Zcyto21 gain or loss of expression may serve as a diagnostic for brain and other cancers. Moreover, analogous to the prostate specific antigen (PSA), increased levels of Zcyto21 polypeptides, or anti-Zcyto21 antibodies in a patient, relative to a normal control can be indicative of brain and other cancers (See, e.g., Mulders, TMT, et al., *Eur. J. Surgical Oncol.* 16:37-41, 1990). Strong Zcyto21 expression in tissue not normally found to express Zcyto21 would serve as a diagnostic of an abnormality in the cell or tissue type, of invasion or metastasis of cancerous liver tissue into non-liver tissue, and could aid a physician in directing further testing or investigation, or aid in directing therapy.

In addition, Zcyto21 polynucleotide probes, anti-Zcyto21 antibodies, and detection the presence of Zcyto21 polypeptides in tissue can be used to assess whether brain or other tissue found to normally express Zcyto21 is present, for example, after surgery involving the excision of a diseased or cancerous liver or neuronal tissue. As such, the polynucleotides, polypeptides, and antibodies of the present invention can be used as an aid to determine whether all tissue is excised after surgery, for example, after surgery for brain and other cancers. In such instances, it is especially important to remove all potentially diseased tissue to maximize recovery from the cancer, and to minimize recurrence. Preferred embodiments include fluorescent, radiolabeled, or calorimetrically labeled anti-Zcyto21 antibodies and Zcyto21 polypeptide binding partners, that can be used histologically or in situ.

Moreover, the activity and effect of Zcyto21 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly M S, et al. Cell 79: 315-328,1994). C57BL6/J mice are treated with an experimental agent either through daily injection of recombinant protein, agonist or antagonist or a one-time injection of recombinant adenovirus. Three days following this treatment, $10^5$ to $10^6$ cells are implanted under the dorsal skin. Alternatively, the cells themselves may be infected with recombinant adenovirus, such as one expressing Zcyto21, before implantation so that the protein is synthesized at the tumor site or intracellularly, rather than systemically. The mice normally develop visible tumors within 5 days. The tumors are allowed to grow for a period of up to 3 weeks; during which time they may reach a size of 1500-1800 mm$^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., Zcyto21, on the ability of the tumor to recruit vasculature and undergo metastasis can thus be assessed. In addition, aside from using adenovirus, the implanted cells can be transiently transfected with Zcyto21. Use of stable Zcyto21 transfectants as well as use of induceable promoters to activate Zcyto21 expression in vivo are known in the art and can be used in this system to assess Zcyto21 induction of metastasis. Moreover, purified Zcyto21 or Zcyto21-conditioned media can be directly injected in to this mouse model, and hence be used in this system. For general reference see, O'Reilly M S, et al. *Cell* 79:315-328, 1994; and Rusciano D, et al. Murine Models of Liver Metastasis. *Invasion Metastasis* 14:349-361, 1995.

Antisense methodology can be used to inhibit Zcyto21 gene transcription to examine the effects of such inhibition in vivo. Polynucleotides that are complementary to a segment of a Zcyto21-encoding polynucleotide (e.g., a polynucleotide as set forth in SEQ ID NO:1) are designed to bind to Zcyto21-encoding mRNA and to inhibit translation of such mRNA. Such antisense oligonucleotides can also be used to inhibit expression of Zcyto21 polypeptide-encoding genes in cell culture.

Most cytokines as well as other proteins produced by activated lymphocytes play an important biological role in cell differentiation, activation, recruitment and homeostasis of cells throughout the body. Zcyto21 and inhibitors of Zcyto21 activity are expected to have a variety of therapeutic applications. These therapeutic applications include treatment of diseases which require immune regulation, including autoimmune diseases such as rheumatoid arthritis, multiple sclerosis, myasthenia gravis, systemic lupus erythematosis, and diabetes. Zcyto21 may be important in the regulation of inflammation, and therefore would be useful in treating rheumatoid arthritis, asthma and sepsis. There may be a role of Zcyto21 in mediating tumorgenesis, whereby a Zcyto21 antagonist would be useful in the treatment of cancer. Zcyto21 may be useful in modulating the immune system, whereby Zcyto21 and Zcyto21 antagonists may be used for reducing graft rejection, preventing graft-vs-host disease, boosting immunity to infectious diseases, treating immunocompromised patients (e.g., HIV+patients), or in improving vaccines.

As an interferon-like polypeptide in tissues of brain, islet, prostate, testis, pituitary, placenta, ovarian tumor, lung tumor, rectal tumor and ovarian tumor, as well as a CD3+ cell line, and a virally infected prostate epithelial cell line, Zcyto21 is useful to modulate viral infection, tumorigeneses and metastatis in these and other tissues. In such cases, the interferon-like molecule can be released by cell at the site of infection or abnormal cell growth, or as a secreted molecule, it can migrate to the site from a distant tissue.

The antiviral properties of Zcyto21 are particularly useful in treating infection with papilloma viruses in vitro and in vivo. For example, tumors caused by human papilloma viruses cause benign tumors (i.e., genital warts) as well as malignant tumors such as squamous-cell carcinomas. Treatment for these conditions commonly is surgery or tissue destruction. Currently, however, some antiviral/immunomodulatory drugs, including interferon alpha, have been shown effective in reduce tumor size. See Baker, G. E et al., *Dermatol. Clin. Apr.* 15: 331-340, 1997. Further, as discussed by Rockley, P. F. et al., (*Pharmacol. Ther.* 65(2): 265-287, 1995), immunologic therapy with interferons can be directed against all sites of infection, including clinical, subclinical, and latent disease. In this example, IFN-alpha, IFN-beta and IFN-gamma have been used successfully as monotherapy as well as in combination with other therapies to treat anogenital condyloma acuminatum. Zcyto21 will be a useful treatment similar to IFN-alpha, IFN-beta and IFN-gamma in this treatment. Further more, there has been a strong association between certain types of human papilloma virus and cervical cancer. Zcyto21 can be used to detect, monitor and treat cervical cancers.

As a small, secreted protein in islet cells Zcyto21 can modulate the growth and differentiation of these cells. Additionally, Zcyto21 may be useful in treating diabetes and immunological conditions related to the growth and differentiation of the cells.

The presence of Zcyto21 in brain and pituitary cells indicates that it may also find use in growth and differentiation of these cells. Further, the molecules of the present invention may be responsible for nutritional homeostasis, including behavioral disorders related to feeding and appetite suppression. Additionally, Zcyto21 molecules may find use in treating reproductive disorders in general.

Zcyto21 polypeptides can be administered alone or in combination with other vasculogenic or angiogenic agents, including VEGF. When using Zcyto21 in combination with an additional agent, the two compounds can be administered simultaneously or sequentially as appropriate for the specific condition being treated.

Zcyto21 will be useful in treating tumorgenesis, and therefore would be useful in the treatment of cancer. A Zcyto21 inhibition of anti-IgM stimulated normal B-cells and a similar effect is observed in B-cell tumor lines suggest that there may be therapeutic benefit in treating patients with the Zcyto21 in order to induce the B cell tumor cells into a less proliferative state. The ligand could be administered in combination with other agents already in use including both conventional chemotherapeutic agents as well as immune modulators such as interferon alpha. Alpha/beta interferons have been shown to be effective in treating some leukemias and animal disease models, and the growth inhibitory effects of interferon-alpha and Zcyto21 may be additive for B-cell tumor-derived cell lines.

The present invention provides a method of reducing proliferation of a neoplastic B or T cells comprising administering to a mammal with a B or T cell neoplasm an amount of a composition of Zcyto21 sufficient to reduce proliferation of the neoplastic B or T cells. Zcyto21 stimulation of lytic NK cells from marrow progenitors and the proliferation of T-cells following activation of the antigen receptors would enhance treatment for patients receiving allogenic marrow transplants, and therefore, Zcyto21 will enhance the generation of anti-tumor responses, with or without the infusion of donor lymphocytes.

In another aspect, the present invention provides a method of reducing proliferation of a neoplastic B or T cells comprising administering to a mammal with a B or T cell neoplasm an amount of a composition of Zcyto21 antagonist sufficient to reducing proliferation of the neoplastic B or T cells. Furthermore, the Zcyto21 antagonist can be a ligand/toxin fusion protein.

A Zcyto21-saporin fusion toxin may be employed against a similar set of leukemias and lymphomas, extending the range of leukemias that can be treated with Zcyto21. Fusion toxin mediated activation of the Zcyto21 receptor provides two independent means to inhibit the growth of the target cells, the first being identical to the effects seen by the ligand alone, and the second due to delivery of the toxin through receptor internalization.

Based on the teachings herein, the interferon-like Zcyto21 molecules of the present invention will be useful to detect, monitor or treat such diverse conditions as hairy cell leukemia, renal cell carcinoma, basal cell carcinoma, malignant melanoma, AIDS-related Kaposi's sarcoma, multiple myeloma, chronic myelogenous leukemia, non-Hodgkin's lymphoma, laryngeal papillomatosis, mycosis fungoides, condyloma acuminata, papillomavirus-induced epidermodysplasi verruciformis, chronic hepatitis B, hepatitis C, chronic hepatitis D, and chronic non-A, non-B/C hepatitis. The U.S. Food and Drug Administration has approved the use of interferon-β to treat multiple sclerosis, a chronic disease of the nervous system. Interferon-γ is used to treat chronic granulomatous diseases, in which the interferon enhances the patient's immune response to destroy infectious bacterial, fungal, and protozoal pathogens. Clinical studies also indicate that interferon-γ may be useful in the treatment of AIDS, leishmaniasis, and lepromatous leprosy.

For pharmaceutical use, Zcyto21 proteins are formulated for topical or parenteral, particularly intravenous or subcutaneous, delivery according to conventional methods. In general, pharmaceutical formulations will include a Zcyto21 polypeptide in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in *Remington: The Science and Practice of Pharmacy*, Gennaro, ed., Mack Publishing Co., Easton, Pa., 19th ed., 1995. Zcyto21 will preferably be used in a concentration of about 10 to 100 µg/ml of total volume, although concentrations in the range of 1 ng/ml to 1000 µg/ml may be used. For topical application, such as for the promotion of wound healing, the protein will be applied in the range of 0.1-10 µg/cm$^2$ of wound area, with the exact dose determined by the clinician according to accepted standards, taking into account the nature and severity of the condition to be treated, patient traits, etc. Determination of dose is within the level of ordinary skill in the art. Dosing is daily or intermittently over the period of treatment. Intravenous administration will be by bolus injection or infusion over a typical period of one to several hours. Sustained release formulations can also be employed. In general, a therapeutically effective amount of Zcyto21 is an amount sufficient to produce a clinically significant change in the treated condition, such as a clinically significant change in hematopoietic or immune function, a significant reduction in morbidity, or a significantly increased histological score.

Zcyto21 proteins, agonists, and antagonists are useful for modulating the expansion, proliferation, activation, differentiation, migration, or metabolism of responsive cell types, which include both primary cells and cultured cell lines. Of particular interest in this regard are hematopoietic cells, mesenchymal cells (including stem cells and mature myeloid and lymphoid cells), endothelial cells, epithelial cells, smooth muscle cells, fibroblasts, hepatocytes, neural cells and embryonic stem cells. Zcyto21 polypeptides are added to tissue culture media for these cell types at a concentration of about 10 pg/ml to about 100 ng/ml. Those skilled in the art will recognize that Zcyto21 proteins can be advantageously combined with other growth factors in culture media.

Within the laboratory research field, Zcyto21 proteins can also be used as molecular weight standards or as reagents in assays for determining circulating levels of the protein, such as in the diagnosis of disorders characterized by over- or under-production of Zcyto21 protein or in the analysis of cell phenotype.

Zcyto21 proteins can also be used to identify inhibitors of their activity. Test compounds are added to the assays disclosed above to identify compounds that inhibit the activity of Zcyto21 protein. In addition to those assays disclosed above, samples can be tested for inhibition of Zcyto21 activity within a variety of assays designed to measure receptor binding or the stimulation/inhibition of Zcyto21-dependent cellular responses. For example, Zcyto21-responsive cell lines can be transfected with a reporter gene construct that is responsive to a Zcyto21-stimulated cellular pathway. Reporter gene constructs of this type are known in the art, and will generally comprise a Zcyto21-activated serum response element (SRE) operably linked to a gene encoding an assayable protein, such as luciferase. Candidate compounds, solutions, mixtures or extracts are tested for the ability to inhibit the activity of Zcyto21 on the target cells as evidenced by a decrease in Zcyto21 stimulation of reporter gene expression. Assays of this type will detect compounds that directly block Zcyto21 binding to cell-surface receptors, as well as compounds that block processes in the cellular pathway subsequent to receptor-ligand binding. In the alternative, compounds or other samples can be tested for direct blocking of Zcyto21 binding to receptor using Zcyto21 tagged with a detectable label (e.g., $^{125}$I, biotin, horseradish peroxidase, FITC, and the like). Within assays of this type, the ability of a test sample to inhibit the binding of labeled Zcyto21 to the receptor is indicative of inhibitory activity, which can be confirmed through secondary assays. Receptors used within binding assays may be cellular receptors or isolated, immobilized receptors.

As used herein, the term "antibodies" includes polyclonal antibodies, monoclonal antibodies, antigen-binding fragments thereof such as F(ab')$_2$ and Fab fragments, single chain antibodies, and the like, including genetically engineered antibodies. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains. Antibodies are defined to be specifically binding if they bind to a Zcyto21 polypeptide or protein with an affinity at least 10-fold greater than the binding affinity to control (non-Zcyto21) polypeptide or protein. The affinity of a monoclonal antibody can be readily determined by one of ordinary skill in the art (see, for example, Scatchard, *Ann. NY Acad. Sci.* 51: 660-672, 1949).

Methods for preparing polyclonal and monoclonal antibodies are well known in the art (see for example, Hurrell, J. G. R., Ed., *Monoclonal Hybridoma Antibodies: Techniques and Applications*, CRC Press, Inc., Boca Raton, Fla., 1982, which is incorporated herein by reference). Of particular interest are generating antibodies to hydrophilic antigenic sites which include, for example, residues 155 (Glu) to 160 (Glu); residues 51 (Lys) to 56 (Ala); residues 50 (Phe) to 55 (Asp); residues 140 (Pro) to 145 (Arg); and residues 154 (Gln) to 159 (Lys); as shown in SEQ ID NO: 2. As would be evident to one of ordinary skill in the art, polyclonal antibodies can be generated from a variety of warm-blooded animals such as horses, cows, goats, sheep, dogs, chickens, rabbits, mice, and rats. The immunogenicity of a Zcyto21 polypeptide may be increased through the use of an adjuvant such as alum (aluminum hydroxide) or Freund's complete or incomplete adjuvant. Polypeptides useful for immunization also include fusion polypeptides, such as fusions of a Zcyto21 polypeptide or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

Alternative techniques for generating or selecting antibodies include in vitro exposure of lymphocytes to Zcyto21 polypeptides, and selection of antibody display libraries in phage or similar vectors (e.g., through the use of immobilized or labeled Zcyto21 polypeptide). Human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

A variety of assays known to those skilled in the art can be utilized to detect antibodies which specifically bind to Zcyto21 polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

Antibodies to Zcyto21 may be used for affinity purification of the protein, within diagnostic assays for determining circulating levels of the protein; for detecting or quantitating soluble Zcyto21 polypeptide as a marker of underlying pathology or disease; for immunolocalization within whole animals or tissue sections, including immunodiagnostic applications; for immunohistochemistry; and as antagonists to block protein activity in vitro and in vivo. Antibodies to Zcyto21 may also be used for tagging cells that express Zcyto21; for affinity purification of Zcyto21 polypeptides and proteins; in analytical methods employing FACS; for screening expression libraries; and for generating anti-idiotypic antibodies. Antibodies can be linked to other compounds, including therapeutic and diagnostic agents, using known methods to provide for targeting of those compounds to cells expressing receptors for Zcyto21. For certain applications, including in vitro and in vivo diagnostic uses, it is advantageous to employ labeled antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies of the present invention may also be directly or indirectly conjugated to drugs, toxins, radionuclides and the like, and these conjugates used for in vivo diagnostic or therapeutic applications (e.g., inhibition of cell proliferation). See, in general, Ramakrishnan et al., *Cancer Res.* 56:1324-1330, 1996.

Polypeptides and proteins of the present invention can be used to identify and isolate receptors. Zcyto21 receptors may be involved in growth regulation in the liver, blood vessel formation, and other developmental processes. For example, Zcyto21 proteins and polypeptides can be immobilized on a column, and membrane preparations run over the column (as generally disclosed in *Immobilized Affinity Ligand Techniques*, Hermanson et al., eds., Academic Press, San Diego, Calif., 1992, pp. 195-202). Proteins and polypeptides can also be radiolabeled (*Methods Enzymol.*, vol. 182, "Guide to Protein Purification", M. Deutscher, ed., Academic Press, San Diego, 1990, 721-737) or photoaffinity labeled (Brunner et al., *Ann. Rev. Biochem.* 62:483-514, 1993 and Fedan et al., *Biochem. Pharmacol.* 33:1167-1180, 1984) and used to tag specific cell-surface proteins. In a similar manner, radiolabeled Zcyto21 proteins and polypeptides can be used to clone the cognate receptor in binding assays using cells transfected with an expression cDNA library.

Zcyto21 polypeptides can also be used to teach analytical skills such as mass spectrometry, circular dichroism, to determine conformation, especially of the four alpha helices, x-ray crystallography to determine the three-dimensional structure in atomic detail, nuclear magnetic resonance spectroscopy to reveal the structure of proteins in solution. For example, a kit containing the Zcyto21 can be given to the student to analyze. Since the amino acid sequence would be known by the instructor, the protein can be given to the student as a test to determine the skills or develop the skills of the student, the instructor would then know whether or not the student has correctly analyzed the polypeptide. Since every polypeptide is unique, the educational utility of Zcyto21 would be unique unto itself.

The antibodies which bind specifically to Zcyto21 can be used as a teaching aid to instruct students how to prepare affinity chromatography columns to purify Zcyto21, cloning and sequencing the polynucleotide that encodes an antibody and thus as a practicum for teaching a student how to design humanized antibodies. The Zcyto21 gene, polypeptide, or antibody would then be packaged by reagent companies and sold to educational institutions so that the students gain skill in art of molecular biology. Because each gene and protein is unique, each gene and protein creates unique challenges and learning experiences for students in a lab practicum. Such educational kits containing the Zcyto21 gene, polypeptide, or antibody are considered within the scope of the present invention. The present invention, thus generally described, will be understood more readily by reference to the following examples, which is provided by way of illustration and is not intended to be limiting of the present invention.

EXAMPLES

Example 1

An expression plasmid containing all or part of a polynucleotide encoding Zcyto21 is constructed via homologous recombination. A fragment of Zcyto21 cDNA is isolated by PCR using the polynucleotide sequence of SEQ ID NO: 1 with flanking regions at the 5' and 3' ends corresponding to the vector sequences flanking the Zcyto21 insertion point. The primers for PCR each include from 5' to 3' end: 40 bp of flanking sequence from the vector and 17 bp corresponding to the amino and carboxyl termini from the open reading frame of Zcyto21.

Ten μl of the 100 μl PCR reaction mixture is run on a 0.8% low-melting-temperature agarose (SeaPlaque GTG®; FMC BioProducts, Rockland, Me.) gel with 1×TBE buffer for analysis. The remaining 90 μl of the reaction misture is precipitated with the addition of 5 μl 1 M NaCl and 250 μl of absolute ethanol. The plasmid pZMP6, which has been cut with SmaI, is used for recombination with the PCR fragment. Plamid pZMP6 is a mammalian expression vector containing an expression cassette having the cytomegalovirus immediate early promoter, multiple restriction sites for insertion of coding sequences, a stop codon, and a human growth hormone terminator; an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*. It was constructed from pZP9 (deposited at the American Type Culture Collection, 10801 University Boulevard, Manassas, Va. 20110-2209, under Accession No. 98668) with the yeast genetic elements taken from pRS316

(deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain.

One hundred microliters of competent yeast (*S. cerevisiae*) cells are independently combined with 10 μl of the various DNA mixtures from above and transferred to a 0.2-cm electroporation cuvette. The yeast/DNA mixtures are electropulsed using power supply (BioRad Laboratories, Hercules, Calif.) settings of 0.75 kV (5 kV/cm), ∞ ohms, 25 μF. To each cuvette is added 600 μl of 1.2 M sorbitol, and the yeast is plated in two 300-μl aliquots onto two URA-D plates and incubated at 30° C. After about 48 hours, the Ura+ yeast transformants from a single plate are resuspended in 1 ml H$_2$O and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 μl acid-washed glass beads and 200 μl phenol-chloroform, vortexed for 1 minute intervals two or three times, and spun for 5 minutes in an Eppendorf centrifuge at maximum speed. Three hundred microliters of the aqueous phase is transferred to a fresh tube, and the DNA is precipitated with 600 μl ethanol (EtOH), followed by centrifugation for 10 minutes at 4° C. The DNA pellet is resuspended in 10 μl H$_2$O.

Transformation of electrocompetent *E. coli* host cells (Electromax DH10B™ cells; obtained from Life Technologies, Inc., Gaithersburg, Md.) is done with 0.5-2 ml yeast DNA prep and 40 μl of cells. The cells are electropulsed at 1.7 kV, 25 μF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) is plated in 250-μl aliquots on four LB AMP plates (LB broth (Lennox), 1.8% Bacto™ Agar (Difco), 100 mg/L Ampicillin).

Individual clones harboring the correct expression construct for Zcyto21 are identified by restriction digest to verify the presence of the Zcyto21 insert and to confirm that the various DNA sequences have been joined correctly to one another. The inserts of positive clones are subjected to sequence analysis. Larger scale plasmid DNA is isolated using a commercially available kit (QIAGEN Plasmid Maxi Kit, Qiagen, Valencia, Calif.) according to manufacturer's instructions. The correct construct is designated pZMP6/Zcyto21.

Example 2

CHO DG44 cells (Chasin et al., *Som. Cell. Molec. Genet.* 12:555-666, 1986) are plated in 10-cm tissue culture dishes and allowed to grow to approximately 50% to 70% confluency overnight at 37° C., 5% CO$_2$, in Ham's F12/FBS media (Ham's F12 medium (Life Technologies), 5% fetal bovine serum (Hyclone, Logan, Utah), 1% L-glutamine (JRH Biosciences, Lenexa, Kans.), 1% sodium pyruvate (Life Technologies)). The cells are then transfected with the plasmid Zcyto21/pZMP6 by liposome-mediated transfection using a 3:1 (w/w) liposome formulation of the polycationic lipid 2,3-dioleyloxy-N-[2(sperminecarboxamido)ethyl]-N,N-dimethyl-1-propaniminium-trifluoroacetate and the neutral lipid dioleoyl phosphatidylethanolamine in membrane-filtered water (Lipofectamine™ Reagent, Life Technologies), in serum free (SF) media formulation (Ham's F12, 10 mg/ml transferrin, 5 mg/ml insulin, 2 mg/ml fetuin, 1% L-glutamine and 1% sodium pyruvate). Zcyto21/pZMP6 is diluted into 15-ml tubes to a total final volume of 640 μl with SF media. 35 μl of Lipofectamine™ is mixed with 605 μl of SF medium. The resulting mixture is added to the DNA mixture and allowed to incubate approximately 30 minutes at room temperature. Five ml of SF media is added to the DNA:Lipofectamine™ mixture. The cells are rinsed once with 5 ml of SF media, aspirated, and the DNA:Lipofectamine™ mixture is added. The cells are incubated at 37° C. for five hours, then 6.4 ml of Ham's F12/10% FBS, 1% PSN media is added to each plate. The plates are incubated at 37° C. overnight, and the DNA:Lipofectamine™ mixture is replaced with fresh 5% FBS/Ham's media the next day. On day 3 post-transfection, the cells are split into T-175 flasks in growth medium. On day 7 postransfection, the cells are stained with FITC-anti-CD8 monoclonal antibody (Pharmingen, San Diego, Calif.) followed by anti-FITC-conjugated magnetic beads (Miltenyi Biotec). The CD8-positive cells are separated using commercially available columns (mini-MACS columns; Miltenyi Biotec) according to the manufacturer's directions and put into DMEM/Ham's F12/5% FBS without nucleosides but with 50 nM methotrexate (selection medium).

Cells are plated for subcloning at a density of 0.5, 1 and 5 cells per well in 96-well dishes in selection medium and allowed to grow out for approximately two weeks. The wells are checked for evaporation of medium and brought back to 200 μl per well as necessary during this process. When a large percentage of the colonies in the plate are near confluency, 100 μl of medium is collected from each well for analysis by dot blot, and the cells are fed with fresh selection medium. The supernatant is applied to a nitrocellulose filter in a dot blot apparatus, and the filter is treated at 100° C. in a vacuum oven to denature the protein. The filter is incubated in 625 mM Tris-glycine, pH 9.1, 5 mM β-mercaptoethanol, at 65° C., 10 minutes, then in 2.5% non-fat dry milk Western A Buffer (0.25% gelatin, 50 mM Tris-HCl pH 7.4, 150 mM NaCl, 5 mM EDTA, 0.05% Igepal CA-630) overnight at 4° C. on a rotating shaker. The filter is incubated with the antibody-HRP conjugate in 2.5% non-fat dry milk Western A buffer for 1 hour at room temperature on a rotating shaker. The filter is then washed three times at room temperature in PBS plus 0.01% Tween 20, 15 minutes per wash. The filter is developed with chemiluminescence reagents (ECL™ direct labelling kit; Amersham Corp., Arlington Heights, Ill.) according to the manufacturer's directions and exposed to film (Hyperfilm ECL, Amersham Corp.) for approximately 5 minutes. Positive clones are trypsinized from the 96-well dish and transferred to 6-well dishes in selection medium for scaleup and analysis by Western blot.

Example 3

Full-length Zcyto21 protein is produced in BHK cells transfected with pZMP6/Zcyto21 (Example 1). BHK 570 cells (ATCC CRL-10314) are plated in 10-cm tissue culture dishes and allowed to grow to approximately 50 to 70% confluence overnight at 37° C., 5% CO$_2$, in DMEM/FBS media (DMEM, Gibco/BRL High Glucose; Life Technologies), 5% fetal bovine serum (Hyclone, Logan, Utah), 1 mM L-glutamine (JRH Biosciences, Lenexa, Kans.), 1 mM sodium pyruvate (Life Technologies). The cells are then transfected with pZMP6/Zcyto21 by liposome-mediated transfection (using Lipofectamine™; Life Technologies), in serum free (SF) media (DMEM supplemented with 10 mg/ml transferrin, 5 mg/ml insulin, 2 mg/ml fetuin, 1%

L-glutamine and 1% sodium pyruvate). The plasmid is diluted into 15-ml tubes to a total final volume of 640 µl with SF media. 35 µl of the lipid mixture is mixed with 605 µl of SF medium, and the resulting mixture is allowed to incubate approximately 30 minutes at room temperature. Five milliliters of SF media is then added to the DNA:lipid mixture. The cells are rinsed once with 5 ml of SF media, aspirated, and the DNA:lipid mixture is added. The cells are incubated at 37° C. for five hours, then 6.4 ml of DMEM/10% FBS, 1% PSN media is added to each plate. The plates are incubated at 37° C. overnight, and the DNA:lipid mixture is replaced with fresh 5% FBS/DMEM media the next day. On day 5 post-transfection, the cells are split into T-162 flasks in selection medium (DMEM+5% FBS, 1% L-Gln, 1% NaPyr, 1 µM methotrexate). Approximately 10 days post-transfection, two 150-mm culture dishes of methotrexate-resistant colonies from each transfection are trypsinized, and the cells are pooled and plated into a T-162 flask and transferred to large-scale culture.

Example 4

For construction of adenovirus vectors, the protein coding region of human Zcyto21 is amplified by PCR using primers that add PmeI and AscI restriction sites at the 5' and 3' termini respectively. Amplification is performed with a full-length Zcyto21 cDNA template in a PCR reaction as follows: one cycle at 95° C. for 5 minutes; followed by 15 cycles at 95° C. for 1 min., 61° C. for 1 min., and 72° C. for 1.5 min.; followed by 72° C. for 7 min.; followed by a 4° C. soak. The PCR reaction product is loaded onto a 1.2% low-melting-temperature agarose gel in TAE buffer (0.04 M Tris-acetate, 0.001 M EDTA). The Zcyto21 PCR product is excised from the gel and purified using a commercially available kit comprising a silica gel mambrane spin column (QIAquick® PCR Purification Kit and gel cleanup kit; Qiagen, Inc.) as per kit instructions. The PCR product is then digested with PmeI and AscI, phenol/chloroform extracted, EtOH precipitated, and rehydrated in 20 ml TE (Tris/EDTA pH 8). The Zcyto21 fragment is then ligated into the PmeI-AscI sites of the transgenic vector pTG12-8 and transformed into E. coli DH10B™ competent cells by electroporation. Vector pTG12-8 was derived from p2999B4 (Palmiter et al., Mol. Cell Biol. 13:5266-5275, 1993) by insertion of a rat insulin II intron (ca. 200 bp) and polylinker (Fse I/Pme I/Asc I) into the Nru I site. The vector comprises a mouse metallothionein (MT-1) promoter (ca. 750 bp) and human growth hormone (hGH) untranslated region and polyadenylation signal (ca. 650 bp) flanked by 10 kb of MT-1 5' flanking sequence and 7 kb of MT-1 3' flanking sequence. The cDNA is inserted between the insulin II and hGH sequences. Clones containing Zcyto21 are identified by plasmid DNA miniprep followed by digestion with PmeI and AscI. A positive clone is sequenced to insure that there were no deletions or other anomalies in the construct.

DNA is prepared using a commercially available kit (Maxi Kit, Qiagen, Inc.), and the Zcyto21 cDNA is released from the pTG12-8 vector using PmeI and AscI enzymes. The cDNA is isolated on a 1% low melting temperature agarose gel and excised from the gel. The gel slice is melted at 70 µC, and the DNA is extracted twice with an equal volume of Tris-buffered phenol, precipitated with EtOH, and resuspended in 10 µl H$_2$O.

The Zcyto21 cDNA is cloned into the EcoRV-AscI sites of a modified pAdTrack-CMV (He, T-C. et al., Proc. Natl. Acad. Sci. USA 95:2509-2514, 1998). This construct contains the green fluorescent protein (GFP) marker gene. The CMV promoter driving GFP expression is replaced with the SV40 promoter, and the SV40 polyadenylation signal is replaced with the human growth hormone polyadenylation signal. In addition, the native polylinker is replaced with FseI, EcoRV, and AscI sites. This modified form of pAdTrack-CMV is named pZyTrack. Ligation is performed using a commercially available DNA ligation and screening kit (Fast-Link® kit; Epicentre Technologies, Madison, Wis.). Clones containing Zcyto21 are identified by digestion of mini prep DNA with FseI and AscI. In order to linearize the plasmid, approximately 5 µg of the resulting pZyTrack Zcyto21 plasmid is digested with PmeI. Approximately 1 µg of the linearized plasmid is cotransformed with 200 ng of supercoiled pAdEasy (He et al., ibid.) into E. coli BJ5183 cells (He et al., ibid.). The co-transformation is done using a Bio-Rad Gene Pulser at 2.5 kV, 200 ohms and 25 µFa. The entire co-transformation mixture is plated on 4 LB plates containing 25 µg/ml kanamycin. The smallest colonies are picked and expanded in LB/kanamycin, and recombinant adenovirus DNA is identified by standard DNA miniprep procedures. The recombinant adenovirus miniprep DNA is transformed into E. coli DH10B™ competent cells, and DNA is prepared using a Maxi Kit (Qiagen, Inc.) according to kit instructions.

Approximately 5 µg of recombinant adenoviral DNA is digested with PacI enzyme (New England Biolabs) for 3 hours at 37° C. in a reaction volume of 100 µl containing 20-30 U of PacI. The digested DNA is extracted twice with an equal volume of phenol/chloroform and precipitated with ethanol. The DNA pellet is resuspended in 10 µl distilled water. A T25 flask of QBI-293A cells (Quantum Biotechnologies, Inc. Montreal, Qc. Canada), inoculated the day before and grown to 60-70% confluence, is transfected with the PacI digested DNA. The PacI-digested DNA is diluted up to a total volume of 50 µl with sterile HBS (150 mM NaCl, 20 mM HEPES). In a separate tube, 20 µl of 1 mg/ml N-[1-(2,3-Dioleoyloxy)propyl]-N,N,N-trimethyl-ammonium salts (DOTAP) (Boehringer Mannheim, Indianapolis, Ind.) is diluted to a total volume of 100 µl with HBS. The DNA is added to the DOTAP, mixed gently by pipeting up and down, and left at room temperature for 15 minutes. The media is removed from the 293A cells and washed with 5 ml serum-free minimum essential medium (MEM) alpha containing 1 mM sodium pyruvate, 0.1 mM MEM non-essential amino acids, and 25 mM HEPES buffer (reagents obtained from Life Technologies, Gaithersburg, Md.). 5 ml of serum-free MEM is added to the 293A cells and held at 37° C. The DNA/lipid mixture is added drop-wise to the T25 flask of 293A cells, mixed gently, and incubated at 37° C. for 4 hours. After 4 hours the media containing the DNA/lipid mixture is aspirated off and replaced with 5 ml complete MEM containing 5% fetal bovine serum. The transfected cells are monitored for GFP expression and formation of foci (viral plaques).

Seven days after transfection of 293A cells with the recombinant adenoviral DNA, the cells express the GFP protein and start to form foci (viral "plaques"). The crude viral lysate is collected using a cell scraper to collect all of the 293A cells. The lysate is transferred to a 50-ml conical tube. To release most of the virus particles from the cells, three freeze/thaw cycles are done in a dry ice/ethanol bath and a 37° C. waterbath.

The crude lysate is amplified (Primary (1°) amplification) to obtain a working "stock" of Zcyto21 rAdV lysate. Ten 10 cm plates of nearly confluent (80-90%) 293A cells are set up 20 hours previously, 200 ml of crude rAdV lysate is added to each 10-cm plate, and the cells are monitored for 48 to 72 hours for CPE (cytopathic effect) under the white light microscope and expression of GFP under the fluorescent microscope. When all of the 293A cells show CPE, this stock lysate is collected and freeze/thaw cycles performed as described above.

A secondary (2°) amplification of Zcyto21 rAdV is then performed. Twenty 15-cm tissue culture dishes of 293A cells are prepared so that the cells are 80-90% confluent. All but 20 ml of 5% MEM media is removed, and each dish is inoculated with 300-500 ml of the 1° amplified rAdv lysate. After 48 hours the 293A cells are lysed from virus production, the lysate is collected into 250-ml polypropylene centrifuge bottles, and the rAdV is purified.

NP-40 detergent is added to a final concentration of 0.5% to the bottles of crude lysate in order to lyse all cells. Bottles are placed on a rotating platform for 10 minutes agitating as fast as possible without the bottles falling over. The debris is pelleted by centrifugation at 20,000×G for 15 minutes. The supernatant is transferred to 250-ml polycarbonate centrifuge bottles, and 0.5 volume of 20% PEG8000/2.5 M NaCl solution is added. The bottles are shaken overnight on ice. The bottles are centrifuged at 20,000×G for 15 minutes, and the supernatant is discarded into a bleach solution. Using a sterile cell scraper, the white, virus/PEG precipitate from 2 bottles is resuspended in 2.5 ml PBS. The resulting virus solution is placed in 2-ml microcentrifuge tubes and centrifuged at 14,000×G in the microcentrifuge for 10 minutes to remove any additional cell debris. The supernatant from the 2-ml microcentrifuge tubes is transferred into a 15-ml polypropylene snapcap tube and adjusted to a density of 1.34 g/ml with CsCl. The solution is transferred to 3.2-ml, polycarbonate, thick-walled centrifuge tubes and spun at 348,000×G for 3-4 hours at 25 µC. The virus forms a white band. Using wide-bore pipette tips, the virus band is collected.

A commercially available ion-exchange columns (e.g., PD-10 columns prepacked with Sephadex® G-25M; Pharmacia Biotech, Piscataway, N.J.) is used to desalt the virus preparation. The column is equilibrated with 20 ml of PBS. The virus is loaded and allowed to run into the column. 5 ml of PBS is added to the column, and fractions of 8-10 drops are collected. The optical densities of 1:50 dilutions of each fraction are determined at 260 nm on a spectrophotometer. Peak fractions are pooled, and the optical density (OD) of a 1:25 dilution is determined. OD is converted to virus concentration using the formula: (OD at 260 nm)(25)(1.1×10$^{12}$) =virions/ml.

To store the virus, glycerol is added to the purified virus to a final concentration of 15%, mixed gently but effectively, and stored in aliquots at −80 µC.

A protocol developed by Quantum Biotechnologies, Inc. (Montreal, Canada) is followed to measure recombinant virus infectivity. Briefly, two 96-well tissue culture plates are seeded with 1×10$^4$ 293A cells per well in MEM containing 2% fetal bovine serum for each recombinant virus to be assayed. After 24 hours 10-fold dilutions of each virus from 1×10$^{-2}$ to 1×10$^{-14}$ are made in MEM containing 2% fetal bovine serum. 100 µl of each dilution is placed in each of 20 wells. After 5 days at 37° C., wells are read either positive or negative for CPE, and a value for "Plaque Forming Units/ml" (PFU) is calculated.

Example 5

Trangenic animals expressing Zcyto21 genes are producing using adult, fertile males (studs) (B6C3fl, 2-8 months of age (Taconic Farms, Germantown, N.Y.)), vasectomized males (duds) (CD1, 2-8 months, (Taconic Farms)), prepubescent fertile females (donors) (B6C3fl, 4-5 weeks, (Taconic Farms)) and adult fertile females (recipients) (CD1, 2-4 months, (Taconic Farms)).

The donors are acclimated for 1 week and then injected with approximately 8 IU/mouse of Pregnant Mare's Serum gonadotrophin (Sigma, St. Louis, Mo.) I.P., and 4647 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope (Leica MZ12 Stereo Microscope, Leica, Wetzlar, Del.). The oviducts are collected and eggs are released into urinanalysis slides containing hyaluronidase (Sigma). Eggs are washed once in hyaluronidase, and twice in Whitten's W640 medium (Table 4) that has been incubated with 5% $CO_2$, 5% $O_2$, and 90% $N_2$ at 37° C. The eggs are then stored in a 37° C./5% $CO_2$ incubator until microinjection.

10-20 micrograms of plasmid DNA containing a cDNA of the Zcyto21 gene is linearized, gel-purified, and resuspended in 10 mM Tris pH 7.4, 0.25 mM EDTA pH 8.0, at a final concentration of 5-10 nanograms per microliter for microinjection.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pregassed W640 medium for storage overnight in a 37° C./5% $CO_2$ incubator.

The following day, 12-17 healthy 2-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa. The embryos are implanted through this nick, and by holding onto the peritoneal wall, the reproductive organs are guided back into the abdominal cavity.

The recipients are returned to cages in pairs, and allowed 19-21 days gestation. After birth, 19-21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using a Qiagen Dneasy kit following the manufacturer's instructions. Genomic DNA is analyzed by PCR using primers designed to the human growth hormone (hGH) 3' UTR portion of the transgenic vector. A region unique to the human sequence was identified from an alignment of the human and mouse growth hormone 3' UTR DNA sequences, ensuring that the PCR reaction does not amplify the mouse sequence. Primers which amplify a 368 base pair fragment of hGH and primers which hybridize to vector sequences and amplify the cDNA insert, are often used along with the hGH primers. In these experiments, DNA from animals positive for the transgene will generate two bands, a 368 base pair band corresponding to the hGH 3' UTR fragment and a band of variable size corresponding to the cDNA insert.

Once animals are confirmed to be transgenic (TG), they may be back-crossed into an inbred strain by placing a TG female with a wild-type male, or a TG male with one or two wild-type female(s). As pups are born and weaned, the sexes are separated, and their tails snipped for genotyping.

Analysis of the mRNA expression level of each transgene is done using an RNA solution hybridization assay or real-time PCR on an ABI Prism 7700 (PE Applied Biosystems, Inc., Foster City, Calif.) following manufacturer's instructions.

TABLE 5

WHITTEN'S 640 MEDIA

|  | mgs/200 m | mgs/500/ml |
|---|---|---|
| NaCl | 1280 | 3200 |
| KCl | 72 | 180 |
| KH$_2$PO$_4$ | 32 | 80 |
| MgSO$_4$.7H$_2$O | 60 | 150 |
| Glucose | 200 | 500 |
| Ca$^{2+}$ Lactate | 106 | 265 |
| K Penn | 15 | 37.5 |
| Streptomycin SO$_4$ | 10 | 25 |
| NaHCO$_3$ | 380 | 950 |
| Na Pyruvate | 5 | 12.5 |
| H$_2$0 | 200 | 500 |
| EDTA | 100 µl | 250 µl |
| 5% Phenol Red | 200 µl | 500 µl |
| BSA | 600 | 1500 |

All reagents are available from Sigma.

Example 6

1. Stimulation of Expression from an Interferon-Responsive Promoter

In one series of experiments, conditioned medium (CM) containing Zcyto21 protein is generated by infecting 293A cells with recombinant adenovirus containing the cDNA for Zcyto21 (AdZy-Zcyto21) at a multiplicity of infection of 400 particles per cell. CM is harvested at time points between 40 hours post infection and stored at −20° C. CM is also generated from an infection with a recombinant adenovirus lacking a cDNA (AdZy-parental). Prior to use, a portion of the CM is concentrated 14 fold in a Millipore Ultrafree-15 (5,000 nominal molecular weight limit) centrifugal filter, and then, filtered through a Millipore Ultrafree-15 (100,000 nominal molecular weight limit) centrifugal filter to reduce the amount of viral particles present in the media, and finally filtered through a Millipore 0.2 µm syringe filter to sterilize the CM. Concentrated CM samples are diluted 1:2 in binding buffer and incubated with cells from a murine cell line for 5 hours at 37° C.

2. Anti-Viral Activity of Zcyto21

Another series of experiments examines the anti-viral activity of Zcyto21. In these studies, the anti-viral assay is performed by plating L929 cells (ATCC No. CCL-1) in growth media RPMI medium 1640 containing 10% fetal bovine serum, penicillin, streptomycin, and L-glutamine in 96-well format at 50,000 cells per well. Adenovirus CM from 293A cells infected with either AdZy-Zcyto21 m or AdZy-parental, as described above, are incubated with cells overnight. A positive control in the assay is provided by murine interferon-α serially diluted 1:10, starting at 100 ng/ml. L929 cells with growth media alone provided the negative control. Treated cells are incubated for 24 hours. The media are discarded, fresh medium are added, and encephalomyocarditis virus (ATCC No. vr129b) is introduced at a multiplicity of infection of 0.1 (i.e., one virus particle for every ten L929 cells). The cells are incubated in the presence of the virus for 24 hours, and then, the wells are scored for percent cytopathic effect (CPE.

3. Antiproliferation Assay Using a BAF3 Cell Line

BaF3 is used to determine if Zcyto21 has anti-proliferative properties. Baby hamster kidney (BHK) cells are stably transfected with an expression vector containing the CMV promoter plus intron A upstream of the Zcyto21 cDNA or an unrelated cDNA, called Zα30, using BRL lipofectamine. Stably transfected cells are seeded in a cell factory in serum free media and allowed to grow for three days before conditioned media is harvested and concentrated in a 5K filter to 10×. Concentrated conditioned medium samples are stored at 4° C.

The following assay is used to test for anti-proliferation of BaF3. In a 96 well plate, eight 1:2 serial dilutions are made of growth media alone (RPMI 1640, 10% fetal bovine serum, 1 mM sodium pyruvate, 2 mM L-glutamine), or murine IL-3 (starting at 50 pg/ml in growth medium) with final volume of 100 µl. Fifty microliters of the following are added to both growth media alone or mIL-3 diluted lanes: human interferon-α (100 ng/ml, 10 ng/ml, or 1 ng/ml diluted in growth medium), human interferon-β (100 ng/ml, 10 ng/ml, or 1 ng/ml diluted in growth medium), murine interferon-α (100 ng/ml, 10 ng/ml, or 1 ng/ml diluted in growth medium), murine interferon-β (100 ng/ml, 10 ng/ml, or 1 ng/ml diluted in growth medium), Zcyto21 (at 2.5×, 0.5×, or 0.1×), and murine Zα30 (at 2.5×, 0.5×, or 0.1×).

The BaF3cell line is washed three times in growth medium, pellets are resuspended in growth medium, cells are counted and diluted in growth medium to 5,000 cells/50 µl. Fifty microliters of diluted cells are then added to each dilution of samples. Assay plates are incubated in a 37° C. incubator for three to four days. Twenty microliters of Alomar blue are then added to each well and the plate are incubated overnight at 37° C. The plates are read on the fluorescent plate reader at excitation wavelength of 544 and emission wavelength 590.

Example 7

Tissue Distribution of Human Zcyto21 in Tissue Panels Using PCR

A panel of cDNA samples from human tissues was screened for Zcyto21 expression using PCR. The panel was made in house and contained 77 marathon cDNA and cDNA samples from various norman and cancerous human tissues and cell lines as shown in Table 6, below. The cDNA samples came from in-house libraries or marathon cDNA preparations of RNA that were prepared in-house, or from a commercial supplier such as Clontech (Palo Alto, Calif.) or Invitrogen (Carlsbad, Calif.). The marathon cDNAs were made using the Marathon cDNA Amplification Kit (Clontech). To assure quality of the panel samples, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA; and (3) a sample was sent to sequencing to check for possible ribosomal or mitochondrial DNA contamination. The panel was set up in a 96-well format that included a human genomic DNA (Clontech) positive control sample. Each well contained approximately 0.2-100 pg/µl of cDNA. The first PCR reactions were set up using oligos ZC39,270 (SEQ ID NO:14) and ZC39,272 (SEQ ID NO:15), Advantage 2 DNA Polymerase Mix (Clontech) and Rediload dye (Research Genetics, Inc., Huntsville, Ala.). The amplification was carried out as follows: 1 cycle at 94° for 1 minute then 35 cycles of 94°, 10 seconds; 67°, 45 seconds and ended with a 3 minute final extension at 72°. The correct DNA fragment size was observed in brain, islet, prostate, testis, pituitary, placenta, ovarian tumor, lung tumor, CD3+ and HPVS. Another PCR reaction was set up using oligos ZC39,270 (SEQ ID NO:14) and ZC39,271 (SEQ ID NO:16), Advangtage 2 DNA Polymerase Mix (Clontech) and Rediload dye (Research Genetics). The amplification was carried out as follows: 1 cycle at 94°, 1 minute then 35 cycles of 94°, 10 seconds; 65°, 30 seconds, 72°, 30 seconds and ended with a 3 minute extension at 72°. The correct DNA fragment size was observed in pituitary, rectal tumor and ovarian tumor.

TABLE 6

| Tissue | #samples tested | Tissue | #samples tested |
|---|---|---|---|
| adrenal gland | 1 | bladder | 1 |
| bone marrow | 3 | brain | 2 |
| cervix | 1 | colon | 1 |
| fetal brain | 3 | fetal heart | 2 |
| fetal kidney | 1 | fetal liver | 2 |
| fetal lung | 1 | fetal skin | 1 |
| heart | 2 | fetal muscle | 1 |
| kidney | 2 | liver | 1 |
| lung | 1 | lymph node | 1 |
| mammary gland | 1 | melanoma | 1 |
| ovary | 1 | pancreas | 1 |
| pituitary | 2 | placenta | 3 |
| prostate | 3 | rectum | 1 |
| salivary gland | 2 | skeletal muscle | 1 |
| small intestine | 1 | spinal cord | 2 |
| spleen | 1 | uterus | 1 |
| stomach | 1 | adipocyte library | 1 |
| testis | 5 | islet | 1 |
| thymus | 1 | prostate SMC | 1 |
| thyroid | 2 | RPMI 1788 | 1 |

TABLE 6-continued

| Tissue | #samples tested | Tissue | #samples tested |
|---|---|---|---|
| | | (ATCC # CCL-156) | |
| trachea | 1 | WI38 | 1 |
| | | (ATCC # CCL-75) | |
| esophageal tumor | 1 | lung tumor | 1 |
| liver tumor | 1 | ovarian tumor | 1 |
| rectal tumor | 1 | stomach tumor | 1 |
| uterine tumor | 2 | CD3+ library selected PBMC's (stimulated) | 1 |
| HaCAT library | 1 | HPV library (ATCC # CRL-2221) | 1 |
| HPVS library (ATCC # CRL-2221) - selected | 1 | MG63 library | 1 |
| K562 (ATCC#CCL-243) | 1 | | |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide comprising an amino acid sequence having at least 95% sequence identity to amino acid residues 20-200 of SEQ ID NO:2, wherein the encoded polypeptide inhibits hepatitis B or C replication.

2. The isolated polypeptide of claim 1 wherein the amino acid sequence has greater than 96% sequence identity to amino acid residues 20-200 of SEQ ID NO:2.

3. The isolated polypeptide of claim 1 wherein the amino acid sequence has greater than 97% sequence identity to amino acid residues 20-200 of SEQ ID NO:2.

4. The isolated polypeptide of claim 1 wherein the amino acid sequence has greater than 98% sequence identity to amino acid residues 20-200 of SEQ ID NO:2.

5. The isolated polypeptide of claim 1 wherein the amino acid sequence has greater than 99% sequence identity to amino acid residues 20-200 of SEQ ID NO:2.

6. The isolated polypeptide of claim 1 wherein the amino acid sequence comprises amino acid residues 20-200 of SEQ ID NO:2.

7. The isolated polypeptide of claim 1 wherein the amino acid sequence is amino acid residues 20-200 of SEQ ID NO:2.

8. The isolated polypeptide of claim 1 wherein the polypeptide inhibits hepatitis B replication.

9. The isolated polypeptide of claim 1 wherein the polypeptide inhibits hepatitis C replication.

10. The isolated polypeptide of claim 1 wherein the polypeptide is recombinant.

11. The isolated polypeptide of claim 10 wherein the recombinant polypeptide is produced in a prokaryotic cell.

12. The isolated polypeptide of claim 11 wherein the recombinant polypeptide is produced in *E. coli*.

13. The isolated polypeptide of claim 10 wherein the recombinant polypeptide is produced in a eukaryotic cell.

14. The isolated polypeptide of claim 13 wherein the recombinant polypeptide is produced in a mammalian cell.

15. The isolated polypeptide of claim 14 wherein the recombinant polypeptide is produced in a Chinese hamster ovary cell.

16. A composition comprising:
an isolated polypeptide of claim 1; and
a pharmaceutically acceptable vehicle.

17. The composition of claim 16 wherein the polypeptide inhibits hepatitis B replication.

18. The composition of claim 16 wherein the polypeptide inhibits hepatitis C replication.

* * * * *

UNITED STATES PATENT AND TRADEMARK OFFICE
CERTIFICATE OF CORRECTION

| | | |
|---|---|---|
| PATENT NO. | : 7,253,261 B2 | Page 1 of 1 |
| APPLICATION NO. | : 10/927815 | |
| DATED | : August 7, 2007 | |
| INVENTOR(S) | : Paul O. Sheppard et al. | |

It is certified that error appears in the above-identified patent and that said Letters Patent is hereby corrected as shown below:

In the Claims:

Claim 1:

Column 63, line 40, delete "encoded".

Signed and Sealed this
Fifteenth Day of November, 2011

David J. Kappos
*Director of the United States Patent and Trademark Office*

SEQUENCE LISTING

<160> NUMBER OF SEQ ID NOS: 16

<210> SEQ ID NO 1
<211> LENGTH: 603
<212> TYPE: DNA
<213> ORGANISM: Homo sapiens
<220> FEATURE:
<221> NAME/KEY: CDS
<222> LOCATION: (1)...(603)

<400> SEQUENCE: 1

```
atg gct gca gct tgg acc gtg gtg ctg gtg act ttg gtg cta ggc ttg      48
Met Ala Ala Ala Trp Thr Val Val Leu Val Thr Leu Val Leu Gly Leu
1               5                   10                  15 gcc gtg gca ggc cct gtc ccc act tcc aag ccc acc aca act ggg aag      96
Ala Val Ala Gly Pro Val Pro Thr Ser Lys Pro Thr Thr Thr Gly Lys
                20                  25                  30 ggc tgc cac att ggc agg ttc aaa tct ctg tca cca cag gag cta gcg     144
Gly Cys His Ile Gly Arg Phe Lys Ser Leu Ser Pro Gln Glu Leu Ala
            35                  40                  45 agc ttc aag aag gcc agg gac gcc ttg gaa gag tca ctc aag ctg aaa     192
Ser Phe Lys Lys Ala Arg Asp Ala Leu Glu Glu Ser Leu Lys Leu Lys
        50                  55                  60 aac tgg agt tgc agc tct cct gtc ttc ccc ggg aat tgg gac ctg agg     240
Asn Trp Ser Cys Ser Ser Pro Val Phe Pro Gly Asn Trp Asp Leu Arg
65                  70                  75                  80 ctt ctc cag gtg agg gag cgc cct gtg gcc ttg gag gct gag ctg gcc     288
Leu Leu Gln Val Arg Glu Arg Pro Val Ala Leu Glu Ala Glu Leu Ala
                85                  90                  95 ctg acg ctg aag gtc ctg gag gcc gct gct ggc cca gcc ctg gag gac     336
Leu Thr Leu Lys Val Leu Glu Ala Ala Ala Gly Pro Ala Leu Glu Asp
```

-continued

```
                        100                     105                     110
gtc cta gac cag ccc ctt cac acc ctg cac cac atc ctc tcc cag ctc        384
Val Leu Asp Gln Pro Leu His Thr Leu His His Ile Leu Ser Gln Leu
            115                     120                     125 cag gcc tgt atc cag cct cag ccc aca gca ggg ccc agg ccc cgg ggc        432
Gln Ala Cys Ile Gln Pro Gln Pro Thr Ala Gly Pro Arg Pro Arg Gly
        130                     135                     140 cgc ctc cac cac tgg ctg cac cgg ctc cag gag gcc ccc aaa aag gag        480
Arg Leu His His Trp Leu His Arg Leu Gln Glu Ala Pro Lys Lys Glu
145                     150                     155                 160 tcc gct ggc tgc ctg gag gca tct gtc acc ttc aac ctc ttc cgc ctc        528
Ser Ala Gly Cys Leu Glu Ala Ser Val Thr Phe Asn Leu Phe Arg Leu
                165                     170                     175 ctc acg cga gac ctc aaa tat gtg gcc gat ggg gac ctg tgt ctg aga        576
Leu Thr Arg Asp Leu Lys Tyr Val Ala Asp Gly Asp Leu Cys Leu Arg
            180                     185                     190 acg tca acc cac cct gag tcc acc tga                                    603
Thr Ser Thr His Pro Glu Ser Thr *
        195                     200

<210> SEQ ID NO 2
<211> LENGTH: 200
<212> TYPE: PRT
<213> ORGANISM: Homo sapiens

<400> SEQUENCE: 2

Met Ala Ala Ala Trp Thr Val Val Leu Val Thr Leu Val Leu Gly Leu
  1               5                  10                  15

Ala Val Ala Gly Pro Val Pro Thr Ser Lys Pro Thr Thr Thr Gly Lys
             20                  25                  30

Gly Cys His Ile Gly Arg Phe Lys Ser Leu Ser Pro Gln Glu Leu Ala
         35                  40                  45

Ser Phe Lys Lys Ala Arg Asp Ala Leu Glu Glu Ser Leu Lys Leu Lys
     50                  55                  60

Asn Trp Ser Cys Ser Ser Pro Val Phe Pro Gly Asn Trp Asp Leu Arg
 65                  70                  75                  80

Leu Leu Gln Val Arg Glu Arg Pro Val Ala Leu Glu Ala Glu Leu Ala
                 85                  90                  95

Leu Thr Leu Lys Val Leu Glu Ala Ala Gly Pro Ala Leu Glu Asp
            100                 105                 110

Val Leu Asp Gln Pro Leu His Thr Leu His His Ile Leu Ser Gln Leu
        115                     120                     125

Gln Ala Cys Ile Gln Pro Gln Pro Thr Ala Gly Pro Arg Pro Arg Gly
    130                     135                     140

Arg Leu His His Trp Leu His Arg Leu Gln Glu Ala Pro Lys Lys Glu
145                     150                     155                 160

Ser Ala Gly Cys Leu Glu Ala Ser Val Thr Phe Asn Leu Phe Arg Leu
                165                     170                     175

Leu Thr Arg Asp Leu Lys Tyr Val Ala Asp Gly Asp Leu Cys Leu Arg
            180                     185                     190

Thr Ser Thr His Pro Glu Ser Thr
        195                     200

<210> SEQ ID NO 3
<211> LENGTH: 600
<212> TYPE: DNA
<213> ORGANISM: Artificial Sequence
<220> FEATURE:
```

<223> OTHER INFORMATION: degenerate sequence
<220> FEATURE:
<221> NAME/KEY: misc_feature
<222> LOCATION: (1)...(600)
<223> OTHER INFORMATION: n = A,T,C or G

<400> SEQUENCE: 3

```
atggcngcng cntggacngt ngtnytngtn acnytngtny tggnytngc ngtngcggn      60
ccngtnccna cnwsnaarcc nacnacnacn ggnaarggnt gycayathgg nmgnttyaar   120
wsnytnwsnc cncargaryt ngcnwsntty aaraargcnm ngaygcnyt ngargarwsn    180
ytnaarytna araaytggws ntgywsnwsn ccngtnttyc cnggnaaytg ggayytnmgn   240
ytnytncarg tnmgngarmg nccngtngcn ytngargcng arytngcnyt nacnytnaar   300
gtnytngarg cngcngcgg nccngcnytn gargaygt

```
tcc gct ggc tgc ctg gag gca tct gtc acc ttc aac ctc ttc cgc ctc    528
Ser Ala Gly Cys Leu Glu Ala Ser Val Thr Phe Asn Leu Phe Arg Leu
            165                 170                 175 ctc acg cga gac ctc aaa tat gtg gcc gat ggg aac ctg tgt ctg aga    576
Leu Thr Arg Asp Leu Lys Tyr Val Ala Asp Gly Asn Leu Cys Leu Arg
        180                 185                 190 acg tca acc cac cct gag tcc acc tga                                603
Thr Ser Thr His Pro Glu Ser Thr *
    195                 200
```

<210> SEQ ID NO 5
<211> LENGTH: 200
<212> TYPE: PRT
<213> ORGANISM: Homo sapiens

<400> SEQUENCE: 5

```
Met Ala Ala Ala Trp Thr Val Val Leu Val Thr Leu Val Leu Gly Leu
 1               5                  10                  15

Ala Val Ala Gly Pro Val Pro Thr Ser Lys Pro Thr Thr Thr Gly Lys
             20                  25                  30

Gly Cys His Ile Gly Arg Phe Lys Ser Leu Ser Pro Gln Glu Leu Ala
         35                  40                  45

Ser Phe Lys Lys Ala Arg Asp Ala Leu Glu Glu Ser Leu Lys Leu Lys
     50                  55                  60

Asn Trp Ser Cys Ser Ser Pro Val Phe Pro Gly Asn Trp Asp Leu Arg
 65                  70                  75                  80

Leu Leu Gln Val Arg Glu Arg Pro Val Ala Leu Glu Ala Glu Leu Ala
                 85                  90                  95

Leu Thr Leu Lys Val Leu Glu Ala Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr
        195                 200
```

<210> SEQ ID NO 6
<211> LENGTH: 856
<212> TYPE: DNA
<213> ORGANISM: Homo sapiens
<220> FEATURE:
<221> NAME/KEY: CDS
<222> LOCATION: (98)...(700)

<400> SEQUENCE: 6

```
aattaccttt tcactttaca cacatcatct tggattgccc attttgcgtg gctaaaaagc     60
agagccatgc cgctggggaa gcagttgcga tttagcc atg gct gca gct tgg acc    115
                                     Met Ala Ala Ala Trp Thr
                                      1               5 gtg gtg ctg gtg act ttg gtg cta ggc ttg gcc gtg gca ggc cct gtc    163
Val Val Leu Val Thr Leu Val Leu Gly Leu Ala Val Ala Gly Pro Val
         10                  15                  20
```

-continued

```
ccc act tcc aag ccc acc aca act ggg aag ggc tgc cac att ggc agg     211
Pro Thr Ser Lys Pro Thr Thr Thr Gly Lys Gly Cys His Ile Gly Arg
        25                  30                  35 ttc aaa tct ctg tca cca cag gag cta gcg agc ttc aag aag gcc agg     259
Phe Lys Ser Leu Ser Pro Gln Glu Leu Ala Ser Phe Lys Lys Ala Arg
    40                  45                  50 gac gcc ttg gaa gag tca ctc aag ctg aaa aac tgg agt tgc agc tct     307
Asp Ala Leu Glu Glu Ser Leu Lys Leu Lys Asn Trp Ser Cys Ser Ser
55                  60                  65                  70 cct gtc ttc ccc ggg aat tgg gac ctg agg ctt ctc cag gtg agg gag     355
Pro Val Phe Pro Gly Asn Trp Asp Leu Arg Leu Leu Gln Val Arg Glu
            75                  80                  85 cgc cct gtg gcc ttg gag gct gag ctg gcc ctg acg ctg aag gtc ctg     403
Arg Pro Val Ala Leu Glu Ala Glu Leu Ala Leu Thr Leu Lys Val Leu
        90                  95                 100 gag gcc gct gct ggc cca gcc ctg gag gac gtc cta gac cag ccc ctt     451
Glu Ala Ala Ala Gly Pro Ala Leu Glu Asp Val Leu Asp Gln Pro Leu
    105                 110                 115 cac acc ctg cac cac atc ctc tcc cag ctc cag gcc tgt atc cag cct     499
His Thr Leu His His Ile Leu Ser Gln Leu Gln Ala Cys Ile Gln Pro
120                 125                 130 cag ccc aca gca ggg ccc agg ccc cgg ggc cgc ctc cac cac tgg ctg     547
Gln Pro Thr Ala Gly Pro Arg Pro Arg Gly Arg Leu His His Trp Leu
135                 140                 145                 150 cac cgg ctc cag gag gcc ccc aaa aag gag tcc gct ggc tgc ctg gag     595
His Arg Leu Gln Glu Ala Pro Lys Lys Glu Ser Ala Gly Cys Leu Glu
            155                 160                 165 gca tct gtc acc ttc aac ctc ttc cgc ctc ctc acg cga gac ctc aaa     643
Ala Ser Val Thr Phe Asn Leu Phe Arg Leu Leu Thr Arg Asp Leu Lys
        170                 175                 180 tat gtg gcc gat ggg aac ctg tgt ctg aga acg tca acc cac cct gag     691
Tyr Val Ala Asp Gly Asn Leu Cys Leu Arg Thr Ser Thr His Pro Glu
    185                 190                 195 tcc acc tga caccccacac cttatttatg cgctgagccc tactccttcc             740
Ser Thr *
    200 ttaatttatt tcctctcacc ctttatttat gaagctgcag ccctgactga gacatagggc   800 tgagtttatt gttttacttt tatacattat gcacaaataa acaacaagga attgga       856

<210> SEQ ID NO 7
<211> LENGTH: 200
<212> TYPE: PRT
<213> ORGANISM: Homo sapiens

<400> SEQUENCE: 7

Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95
```

-continued

```
Leu Thr Leu Lys Val Leu Glu Ala Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr
            195                 200
```

<210> SEQ ID NO 8
<211> LENGTH: 676
<212> TYPE: DNA
<213> ORGANISM: Homo sapiens
<220> FEATURE:
<221> NAME/KEY: CDS
<222> LOCATION: (17)...(676)

<400> SEQUENCE: 8

```
gccctcggcc aattgg atg gtg ccc acc aca ttg gca gag cca tgc cgc tgg      52
               Met Val Pro Thr Thr Leu Ala Glu Pro Cys Arg Trp
                 1               5                  10 gga agc agt tgc gat tta gcc atg gct gca gct tgg acc gtg gtg ctg     100
Gly Ser Ser Cys Asp Leu Ala Met Ala Ala Ala Trp Thr Val Val Leu
             15                  20                  25 gtg act ttg gtg cta ggc ttg gcc gtg gca ggc cct gtc ccc act tcc     148
Val Thr Leu Val Leu Gly Leu Ala Val Ala Gly Pro Val Pro Thr Ser
         30                  35                  40 aag ccc acc aca act ggg aag ggc tgc cac att ggc agg ttc aaa tct     196
Lys Pro Thr Thr Thr Gly Lys Gly Cys His Ile Gly Arg Phe Lys Ser
 45                  50                  55                  60 ctg tca cca cag gag cta gcg agc ttc aag aag gcc agg gac gcc ttg     244
Leu Ser Pro Gln Glu Leu Ala Ser Phe Lys Lys Ala Arg Asp Ala Leu
                 65                  70                  75 gaa gag tca ctc aag ctg aaa aac tgg agt tgc agc tct cct gtc ttc     292
Glu Glu Ser Leu Lys Leu Lys Asn Trp Ser Cys Ser Ser Pro Val Phe
             80                  85                  90 ccc ggg aat tgg gac ctg agg ctt ctc cag gtg agg gag cgc cct gtg     340
Pro Gly Asn Trp Asp Leu Arg Leu Leu Gln Val Arg Glu Arg Pro Val
         95                 100                 105 gcc ttg gag gct gag ctg gcc ctg acg ctg aag gtc ctg gag gcc gct     388
Ala Leu Glu Ala Glu Leu Ala Leu Thr Leu Lys Val Leu Glu Ala Ala
    110                 115                 120 gct ggc cca gcc ctg gag gac gtc cta gac cag ccc ctt cac acc ctg     436
Ala Gly Pro Ala Leu Glu Asp Val Leu Asp Gln Pro Leu His Thr Leu
125                 130                 135                 140 cac cac atc ctc tcc cag ctc cag gcc tgt atc cag cct cag ccc aca     484
His His Ile Leu Ser Gln Leu Gln Ala Cys Ile Gln Pro Gln Pro Thr
                145                 150                 155 gca ggg ccc agg ccc cgg ggc cgc ctc cac cac tgg ctg cac cgg ctc     532
Ala Gly Pro Arg Pro Arg Gly Arg Leu His His Trp Leu His Arg Leu
            160                 165                 170 cag gag gcc ccc aaa aag gag tcc gct ggc tgc ctg gag gca tct gtc     580
Gln Glu Ala Pro Lys Lys Glu Ser Ala Gly Cys Leu Glu Ala Ser Val
        175                 180                 185
```

```
acc ttc aac ctc ttc cgc ctc ctc acg cga gac ctc aaa tat gtg gcc    628
Thr Phe Asn Leu Phe Arg Leu Leu Thr Arg Asp Leu Lys Tyr Val Ala
    190                 195                 200 gat ggg gac ctg tgt ctg aga acg tca acc cac cct gag tcc acc tga    676
Asp Gly Asp Leu Cys Leu Arg Thr Ser Thr His Pro Glu Ser Thr *
205                 210                 215
```

<210> SEQ ID NO 9
<211> LENGTH: 219
<212> TYPE: PRT
<213> ORGANISM: Homo sapiens

<400> SEQUENCE: 9

```
Met Val Pro Thr Thr Leu Ala Glu Pro Cys Arg Trp Gly Ser Ser Cys
 1               5                  10                  15

Asp Leu Ala Met Ala Ala Ala Trp Thr Val Leu Val Thr Leu Val
            20                  25                  30

Leu Gly Leu Ala Val Ala Gly Pro Val Pro Thr Ser Lys Pro Thr Thr
        35                  40                  45

Thr Gly Lys Gly Cys His Ile Gly Arg Phe Lys Ser Leu Ser Pro Gln
50                  55                  60

Glu Leu Ala Ser Phe Lys Lys Ala Arg Asp Ala Leu Glu Glu Ser Leu
65                  70                  75                  80

Lys Leu Lys Asn Trp Ser Cys Ser Ser Pro Val Phe Pro Gly Asn Trp
                85                  90                  95

Asp Leu Arg Leu Leu Gln Val Arg Glu Arg Pro Val Ala Leu Glu Ala
            100                 105                 110

Glu Leu Ala Leu Thr Leu Lys Val Leu Glu Ala Ala Gly Pro Ala
        115                 120                 125

Leu Glu Asp Val Leu Asp Gln Pro Leu His Thr Leu His His Ile Leu
130                 135                 140

Ser Gln Leu Gln Ala Cys Ile Gln Pro Gln Pro Thr Ala Gly Pro Arg
145                 150                 155                 160

Pro Arg Gly Arg Leu His His Trp Leu His Arg Leu Gln Glu Ala Pro
                165                 170                 175

Lys Lys Glu Ser Ala Gly Cys Leu Glu Ala Ser Val Thr Phe Asn Leu
            180                 185                 190

Phe Arg Leu Leu Thr Arg Asp Leu Lys Tyr Val Ala Asp Gly Asp Leu
        195                 200                 205

Cys Leu Arg Thr Ser Thr His Pro Glu Ser Thr
210                 215
```

<210> SEQ ID NO 10
<211> LENGTH: 660
<212> TYPE: DNA
<213> ORGANISM: Artificial Sequence
<220> FEATURE:
<223> OTHER INFORMATION: degenerate sequence
<220> FEATURE:
<221> NAME/KEY: misc_feature
<222> LOCATION: (1)...(660)
<223> OTHER INFORMATION: n = A,T,C or G

<400> SEQUENCE: 10

```
atggtnccna cnacnytngc ngarccntgy mgntggggnw snwsntgyga yytngcnatg     60
gcngcngcnt ggacngtngt nytngtnacn ytngtnytng gnytngcngt ngcnggnccn    120
gtnccnacnw snaarccnac nacnacnggn aarggntgyc ayathggnmg nttyaarwsn    180
```

| | | |
|---|---|---|
| ytnwsnccnc argarytngc nwsnttyaar aargcnmgng aygcnytnga rgarwsnytn | 240 | |
| aarytnaara aytggwsntg ywsnwsnccn gtnttyccng gnaaytggga yytnmgnytn | 300 | |
| ytncargtnm mngarmgncc ngtngcnytn gargcngary tngcnytnac nytnaargtn | 360 | |
| ytngargcng cngcnggncc ngcnytngar gaygtnytng aycarccnyt ncayacnytn | 420 | |
| caycayathy tnwsncaryt ncargcntgy athcarccnc arccnacngc nggnccnmgn | 480 | |
| ccnmgngg <210> SEQ ID NO 12
<211> LENGTH: 203
<212> TYPE: PRT
<213> ORGANISM: Homo sapiens

<400> SEQUENCE: 12

Met Val Pro Thr Thr Leu Ala Trp Thr Val Leu Val Thr Leu Val
1               5                   10                  15

Leu Gly Leu Ala Val Ala Gly Pro Val Pro Thr Ser Lys Pro Thr Thr
                20                  25                  30

Thr Gly Lys Gly Cys His Ile Gly Arg Phe Lys Ser Leu Ser Pro Gln
            35                  40                  45

Glu Leu Ala Ser Phe Lys Lys Ala Arg Asp Ala Leu Glu Glu Ser Leu
    50                  55                  60

Lys Leu Lys Asn Trp Ser Cys Ser Ser Pro Val Phe Pro Gly Asn Trp
65                  70                  75                  80

Asp Leu Arg Leu Leu Gln Val Arg Glu Arg Pro Val Ala Leu Glu Ala
                85                  90                  95

Glu Leu Ala Leu Thr Leu Lys Val Leu Glu Ala Ala Gly Pro Ala
                100                 105                 110

Leu Glu Asp Val Leu Asp Gln Pro Leu His Thr Leu His His Ile Leu
            115                 120                 125

Ser Gln Leu Gln Ala Cys Ile Gln Pro Gln Pro Thr Ala Gly Pro Arg
    130                 135                 140

Pro Arg Gly Arg Leu His His Trp Leu His Arg Leu Gln Glu Ala Pro
145                 150                 155                 160

Lys Lys Glu Ser Ala Gly Cys Leu Glu Ala Ser Val Thr Phe Asn Leu
                165                 170                 175

Phe Arg Leu Leu Thr Arg Asp Leu Lys Tyr Val Ala Asp Gly Asp Leu
                180                 185                 190

Cys Leu Arg Thr Ser Thr His Pro Glu Ser Thr
            195                 200

<210> SEQ ID NO 13
<211> LENGTH: 612
<212> TYPE: DNA
<213> ORGANISM: Artificial Sequence
<220> FEATURE:
<223> OTHER INFORMATION: degenerate sequence
<220> FEATURE:
<221> NAME/KEY: misc_feature
<222> LOCATION: (1)...(612)
<223> OTHER INFORMATION: n = A,T,C or G

<400> SEQUENCE: 13
atggtnccna cnacnytngc ntggacngtn gtnytngtna cnytngtnyt nggnytngcn    60
gtngcnggnc cngtnccnac nwsnaarccn acnacnacng gnaarggntg ycayathggn   120
mgnttyaarw snytnwsncc ncargarytn gcnwsnttya araargcnmg ngaygcnytn   180
gargarwsny tnaarytnaa raaytggwsn tgywsnwsnc cngtnttycc nggnaaytgg   240
gayytnmgny tnytncargt nmgngarmgn ccngtngcny tngargcnga rytngcnytn   300
acnytnaarg tnytngargc ncngcnggn ccngcnytng argaygtnyt ngaycarccn   360
ytncayacny tncaycayat hytnwsncar ytncargcnt gyathcarcc ncarccnacn   420
gcnggnccnm gnccnmgngg nmgnytncay caytggytnc aymgnytnca rgargcnccn   480
aaraargarw sngcnggntg yytngargcn wsngtnacnt tyaayytntt ymgnytnytn   540

-continued

```
acnmgngayy tnaartaygt ngcngayggn gayytntgyy tnmgnacnws nacncayccn        600
garwsnacnt rr                                                            612
```

<210> SEQ ID NO 14
<211> LENGTH: 23
<212> TYPE: DNA
<213> ORGANISM: Artificial Sequence
<220> FEATURE:
<223> OTHER INFORMATION: oligonucleotide ZC39270

<400> SEQUENCE: 14

```
aggcggaaga ggttgaaggt gac                                                 23
```

<210> SEQ ID NO 15
<211> LENGTH: 22
<212> TYPE: DNA
<213> ORGANISM: Artificial Sequence
<220> FEATURE:
<223> OTHER INFORMATION: oligonucleotide ZC39272

<400> SEQUENCE: 15

```
cgtcctagac cagccccttc ac                                                  22
```

<210> SEQ ID NO 16
<211> LENGTH: 22
<212> TYPE: DNA
<213> ORGANISM: Artificial Sequence
<220> FEATURE:
<223> OTHER INFORMATION: oligonucleotide ZC39271

<400> SEQUENCE: 16

```
gaccgtggtg ctggtgactt tg                                                  22
```